United States Patent [19]

Siegel et al.

[11] Patent Number: 5,102,789
[45] Date of Patent: Apr. 7, 1992

[54] **PRODUCTION OF EPIDERAMAL GROWTH FACTOR IN *PICHIA PASTORIS* YEAST CELLS**

[75] Inventors: Robert S. Siegel, San Diego; Richard G. Buckholz, Encinitas; Gregory P. Thill; Lillian M. Wondrack, both of San Diego, all of Calif.

[73] Assignee: The Salk Institute Biotechnology/Industrial Associates, Inc., San Diego, Calif.

[21] Appl. No.: 323,964

[22] Filed: Mar. 15, 1989

[51] Int. Cl.$^5$ ............... C07H 15/12; C12P 21/00; C12P 21/02

[52] U.S. Cl. ............... 435/69.4; 435/69.8; 435/69.9; 435/172.3; 435/320.1; 435/255; 435/256; 536/27; 935/37; 935/47; 935/48

[58] Field of Search ............... 435/69.1, 172.3, 255, 435/256, 320, 69.8, 69.9; 935/37, 47, 48; 536/27

[56] References Cited

U.S. PATENT DOCUMENTS

| 4,743,679 | 5/1988 | Cohen et al. | 435/69.1 |
| 4,777,242 | 10/1988 | Nelles et al. | 435/69.1 |
| 4,783,412 | 11/1988 | Bell et al. | 435/69.1 |

FOREIGN PATENT DOCUMENTS

| 0046039 | 7/1982 | European Pat. Off. |
| 0123289 | 10/1984 | European Pat. Off. |
| 0128733 | 12/1984 | European Pat. Off. |
| 0131868 | 1/1985 | European Pat. Off. |
| 0177915 | 4/1986 | European Pat. Off. |
| 0226752 | 1/1987 | European Pat. Off. |
| 8304030 | 11/1983 | PCT Int'l Appl. |
| 8500369 | 1/1985 | PCT Int'l Appl. |
| 8602271 | 4/1986 | PCT Int'l Appl. |
| 2162851 | 2/1986 | United Kingdom |

OTHER PUBLICATIONS

Shaw et al., *Chem. Abst.* 1988, No. 144692y, "Regulated Secretion of MuGM-CSR in *Saccharomyces cerdevisiae* "Gall:MR. Alpha.1 preproseyquences.
Shuster, J., Yeat Genetic Enginering Barr et al. (editors), Butterworth, Stoneham, MA, 1989, pp. 83,97-99 and 108.
Salerno, J. Abstract of Papers, 199th ACS Moeting, Boston, 4/1990, Abstract No. 33.
Brake et al., *Proc Natl. Acad. Sci. U.S.A.* 81, 4642 (1984).
Urdea et al., *Proc. Natl. Acad. Sci U.S.A.* 80, 7461 (1983).
Smith et al., *Nucleic Acids Research* 15, 4467 (1982).
Bell et al., *Nucleic Acids Research* 14, 8427 (1986).
Cregg et al., *Bio/Technology* 5, 479 (1987).
Tschopp et al., *Bio/Technology* 5, 1305 (1987).
Digan et al., *Developments in Industrial Microbiology* 29, 591 (1988).
Gregory et al., *Nature* 257 325 (1975).
Derwent Abstract of Japan 63 202387, 8/22/88.
Derwent Abstract of Japan 63 003791, 1/8/88.
Derwent Abstract of Japan 63 003790, 1/8/88.

*Primary Examiner*—Robin L. Teskin
*Attorney, Agent, or Firm*—Fitch, Even, Tabin & Flannery

[57] ABSTRACT

Epidermal Growth Factor (EGF) is produced by recombinant DNA technology in *Pichia pastoris* yeast cells.

44 Claims, 19 Drawing Sheets

```
        Nco I        10         20         30         40         50         60
          ↓           *          *          *          *          *          *
         CATGGCTAAAACCGCTATCGCTATCACTGTTGCTCTGGCTGGTTTCGCTACCGTTGCTCA
             CGATTTTGGCGATAGCGATAGTGACAACGAGACCGACCAAAGCGATGGCAACGAGT
                  Nla III
```

```
  mature    70         80         90        100        110        120
  protein    *          *          *          *          *          *
        ┌─
    GGCG│AATTCCGATAGCGAGTGTCCTCTGAGTCACGATGGTTACTGTCTACATGACGGCGT
    CCGC│TTAAGGCTATCGCTCACAGGAGACTCAGTGCTACCAATGACAGATGTACTGCCGCA
         EcoR I                   Dde I    Mnl I      Acc I      Aha I
         EcoR I                   Hinf I              Hga I      HgiD I
        EcoR I*                                                  Nla III
                                                                 Tth111I
```

```
         130        140        150        160        170        180
          *          *          *          *          *          *
         CTGTATGTATATTGAGGCTCTAGACAAGTACGCGTGTAATTGCGTTGTTGGCTACATCGG
         GACATACATATAACTCCGAGATCTGTTCATGCGCACATTAACGCAACAACCGATGTAGCC
          Mnl I      Xba I      Mlu I     EcoR I*
                                Rsa I
                                 Tha I
```

```
         190        200        210        220                 Hind III
          *          *          *          *                     ↓
         TGAGCGTTGTCAGTATCGTGATCTGAAATGGTGGGAACTTCGTTAA
         ACTCGCAACAGTCATAGCACTAGACTTTACCACCCTTGAAGCAATTTCGA
          Hph I      Dpn I
                     Mbo I
                     Sau 3A
```

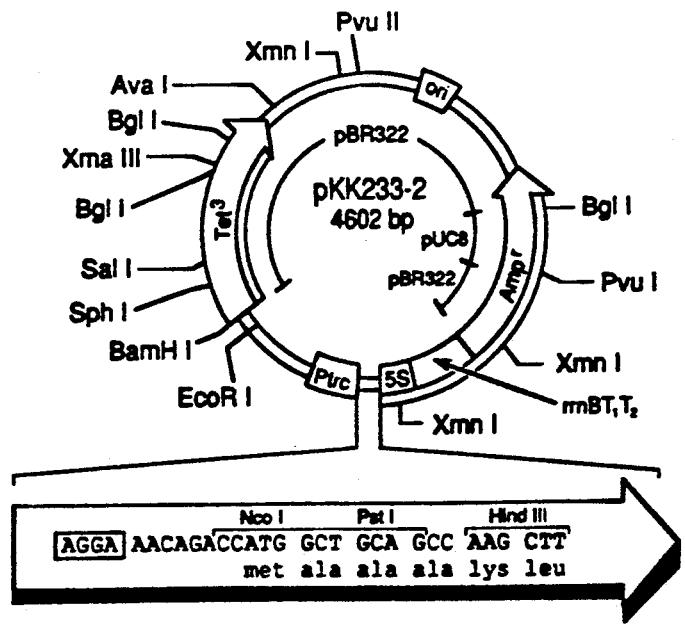

αMF-SUC2 Fusion vector for *S. cerevisiae*
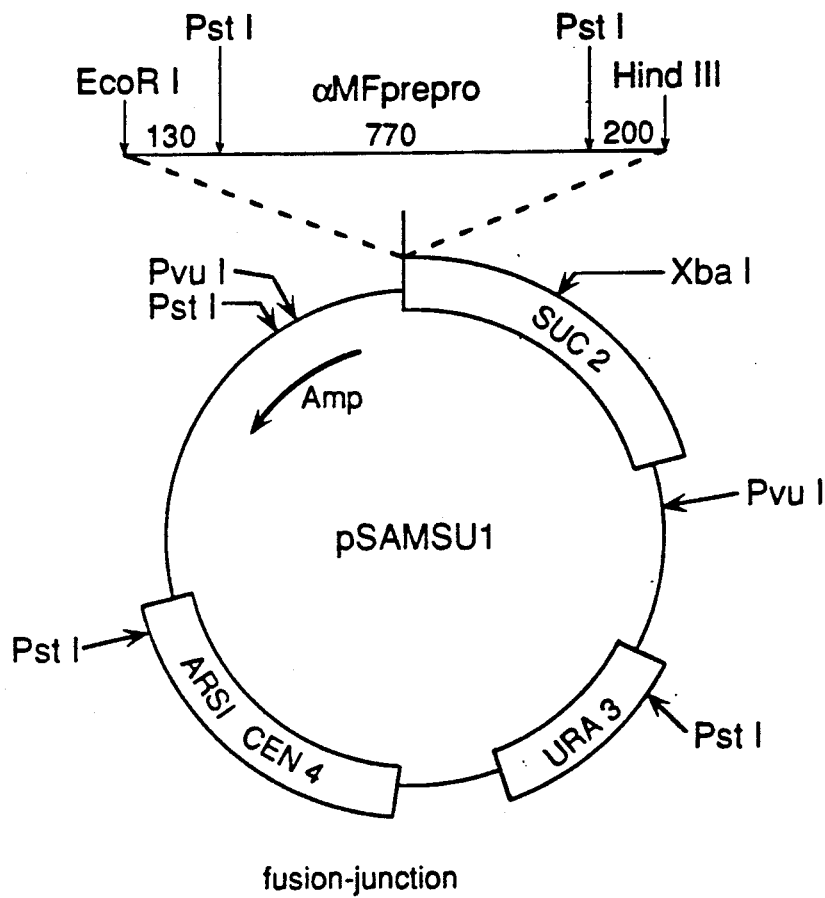
fusion-junction
```
αMFprepro                Hind III                    SUC 2
... AAA AGA GAG GCT GAA GCT TTG ACA AAC GAA ACT AGC GAT AGA ...
... lys arg glu ala glu ala|leu|thr asn glu thr ser asp arg ...
```
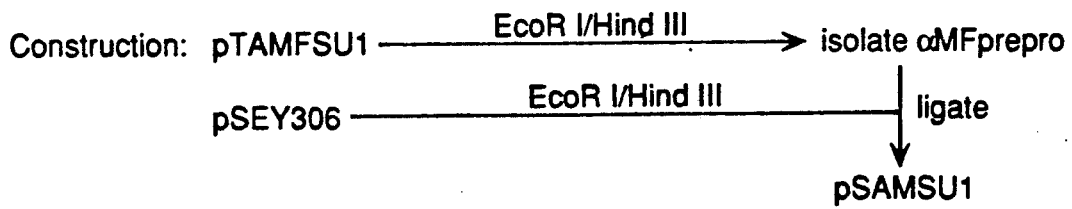
Figure 16

αMF-SUC2 Fusion Vector for *P. pastoris* fusion-junction

```
     αMFprepro           Hind III                          SUC 2
...AAA AGA GAG GCT GAA GCT TTG ACA AAC GAA ACT AGC GAT AGA...
...lys arg glu ala glu ala leu thr asn glu thr ser asp arg...
                              3   4
```

Construction: pSAMSU1 —Pvu I/Pvu II→ isolate fragment (αmF-SUC2)

pYJ30 —EcoR I→ fill in —Pvu I→ isolate HIS4 fragment —ligate→ pSAMSU2

PRODUCTION OF EPIDERAMAL GROWTH FACTOR IN *PICHIA PASTORIS* YEAST CELLS

FIELD OF THE INVENTION

This invention relates to a process of recombinant DNA technology for producing epidermal growth factor (EGF) peptides in *Pichia pastoris* yeast cells. *Pichia pastoris* transformants containing in their genome at least one copy of a DNA sequence operably encoding EGF under the regulation of a promoter region of a *P. pastoris* gene and the *S. cerevisiae* alpha-mating factor (AMF) pre-pro sequence are cultured under conditions allowing the expression of EGF peptides into the culture medium. The invention further relates to the *P. pastoris* transformants, DNA fragments and expression vectors used for their production and cultures containing same.

BACKGROUND OF THE INVENTION

Epidermal growth factor (EGF) is a naturally-occurring, relatively short, single-chain polypeptide, which was first isolated from the mouse submaxillary gland. A structurally very similar polypeptide was later detected and isolated from human urine at low (about 30 ng/ml) concentrations. Both mouse and human epidermal growth factors (the latter one also called urogastrone in some earlier publications) contain 53 amino acids. Thirty-seven of these are identical in the amino acid sequences of mouse epidermal growth factor (mEGF) and human epidermal growth factor (hEGF), as are the relative positions of the three disulfide bonds present in the structure. [Gregory, *Nature*, 257, 325 (1975); Gregory et al., *Hoppe-Seyler's Z. Physiol. Chem.*, 356, 1765 (1975)]. The amino acid sequence of the 53 amino acid containing hEGF (β-hEGF), as reported in the literature, is as follows:

```
Asn Ser Asp Ser Glu Cys Pro Leu Ser His Asp Gly
Tyr Cys Leu His Asp Gly Val Cys Met Tyr Ile Glu
Ala Leu Asp Lys Tyr Ala Cys Asn Cys Val Val Gly
Tyr Ile Gly Glu Arg Cys Gln Tyr Arg Asp Leu Lys
Trp Trp Glu Leu Arg
```

The polypeptide also exists as a 52 amino acid form (gamma-hEGF) that lacks the C-terminal arginine residue found in βhEGF.

The amino acid and nucleotide sequences of hEGF are, for example, disclosed in Hollenberg, "Epidermal Growth Factor-Urogastrone, A Polypeptide Acquiring Hormonal States"; eds., Academic Press, Inc., New York (1979), pp. 69–110; or Urdea et al., Proc. Natl. Acad. Sci. USA. 80, 7461 (1983).

A 48 amino acid containing form of hEGF (lacking C-terminal 5 amino acids) is described in the Japanese Patent Application 86146964, published 8 Feb. 1988 under No. 63003791.

The molecule in natural form contains disulfide linkages between residues 6-20, 14-31 and 33-42, and arises from an about 1200 amino acid precursor molecule consisting of eight EGF-like regions [see e.g. Bell et al., *Nucleic Acid Research*, 14, 21, 8427 (1986)]. A 48 amino acid containing form of rat EGF has recently been disclosed in the Japanese Patent Application 8736498, published 22 Aug. 1988, under No. 63202387. Both mEGF and hEGF, as well as their known analogs, exhibit similar pharmacological activities, although the extent or spectrum of activity may be different for different materials. In general EGF inhibits the secretion of gastric acid and promotes cell growth; therefore, it is targeted for therapeutic potential as an anti-ulcer agent and in external wound healing.

Since isolation from natural source is technically difficult, expensive, and time consuming, recent efforts have centered on the development of efficient recombinant methods for the production of EGF.

Of the hosts widely used for the production of heterologous proteins, probably *E. coli* and *Saccharomyces cerevisiae* (Baker's yeast) are the best understood. However, *E. coli* tends to produce EGF in its reduced form which is not stable in the presence of endogenous bacterial proteases. Attempts to overcome this problem, e.g. by employing a suitable leader sequence in order to produce an insoluble fusion protein which can be readily recovered from the cell paste resulted in other inconveniences, especially during purification of the product.

Yeasts can offer clear advantages over bacteria in the production of heterologous proteins, which include their ability to secrete heterologous proteins into the culture medium. Secretion of proteins from cells is generally superior to production of proteins in the cytoplasm. Secreted products are obtained in a higher degree of initial purity and their further purification is easier to contend with without cellular debris. In the case of sulfhydryl-rich proteins there is another compelling reason for the development of hosts capable of secreting them into the culture medium: their correct tertiary structure is produced and maintained via disulfide bonds. The secretory pathway of the cell and the extracellular medium are oxidizing environments which can support disulfide bond formation [Smith, et al., *Science*, 229, 1219 (1985)]. In contrast, the cytoplasm is a reducing environment in which disulfide bonds cannot form. Upon cell breakage, too rapid formation of disulfide linkages can result in random disulfide bond formation. Consequently, production of sulfhydryl rich proteins, such as EGF, containing appropriately formed disulfide bonds can be best achieved by transit through the secretory pathway.

Secretion of authentic biologically active human epidermal growth factor from *S. cerevisiae* is disclosed in European Patent Application Nos. 84104445.6 and 84303783.9, published Oct. 31, 1984 (No. 0 123 289) and Dec. 19, 1984 (No. 0 128 733), respectively. The cited patent applications contain no details as to the level of secretion or the purity of hEGF obtained. In an article published in *Proc. Natl. Acad. Sci. USA*, 81. 4642 (1984) Brake, inventor of the European Patent Application No. 84104445.6, and his co-workers give more details of their laboratory-scale experiments. hEGF is produced in *S. cerevisiae* by means of an expression cassette containing a DNA sequence encoding mature hEGF joined to sequences encoding the leader region ("pre-pro" segment) of the precursor of the yeast mating pheromone alpha-factor. In what appears to be the best experiment, hEGF was secreted into the shake flask culture medium in a concentration of about 4000 ng/ml. In view of the problems usually encountered with up-scaling the production of heterologous proteins in plasmid-based yeast systems, such as *S. cerevisiae*, there is no indication that hEGF production in *S. cerevisiae* could be at levels higher than those of that experimental system.

According to the prior art methods hEGF is produced and secreted from yeast in mature, usually 52 amino acid containing form.

To overcome the major problems associated with *S. cerevisiae*, e.g. loss of selection for plasmid maintenance and problems concerning plasmid distribution, copy number and stability in fermentors operated at high cell density, a yeast expression system based on the methylotrophic yeast *Pichia pastoris* has been developed. A key feature making this system unique lies with the promoter employed to drive heterologous gene expression. This promoter, which is derived from the methanol-regulated alcohol oxidase I (AOX1) gene of *P. pastoris*, is highly expressed and tightly regulated (see e.g. the European Patent Application No. 85113737.2, published June 4, 1986, under No. 0 183 071). Another key feature of the *P. pastoris* expression system is the stable integration of expression cassettes into the *P. pastoris* genome, thus significantly decreasing the chance of vector loss.

Although *P. pastoris* has been used successfully for the production of various heterologous proteins, e.g., hepatitis B surface antigen [Cregg et al., *Bio/Technology* 5, 479 (1987)], lysozyme and invertase [Digan et al., *Developments in Industrial Microbiology* 29, 59 (1988); Tschopp et al., *Bio/Technology* 5, 1305 (1987)], endeavors to produce other heterologous gene products in Pichia, especially by secretion, have given mixed results. At our present level of understanding of the *P. pastoris* expression system, it is unpredictable whether a given gene can be expressed to an appreciable level in this yeast or whether Pichia will tolerate the presence of the recombinant gene product in its cells. Further, it is especially difficult to foresee if a particular protein will be secreted by *P. pastoris*, and if it is, at what efficiency. Even for *S. cerevisiae*, which has been considerably more extensively studied than *P. pastoris*, the mechanism of protein secretion is not well defined and understood.

SUMMARY OF THE INVENTION

The present invention provides a powerful method for the production of secreted EGF peptides in *Pichia pastoris*, which can be easily scaled up from shake-flask cultures to large fermentors with no loss in productivity and without making major changes in the fermentation conditions. *Pichia pastoris* is a known industrial yeast strain that is capable of utilizing methanol as the sole carbon and energy source (methylotroph). We have surprisingly found that EGF peptides can be produced in and secreted from *P. pastoris* very efficiently, by integrating into the yeast genome at least one copy of a DNA sequence operably encoding EGF in *P. pastoris*, operably associated with DNA encoding the *S. cerevisiae* alpha-mating factor (AMF) pre-pro sequence, both under the regulation of a promoter region of a *P. pastoris* gene. *P. pastoris* cells containing in their genome at least one copy of these segments efficiently produce biologically active EGF peptides as a medium secreted product.

Accordingly, this invention relates to a *P. pastoris* cell containing in its genome at least one copy of a DNA sequence operably encoding an EGF peptide in *P. pastoris* operably associated with the DNA encoding *S. cerevisiae* AMF pre-pro sequence, both under the regulation of a promoter region of a *P. pastoris* gene.

According to another aspect, this invention relates to a DNA fragment containing at least one copy of an expression cassette comprising in the reading frame direction of transcription, a promoter region of a first *P. pastoris* gene, DNA encoding the *S. cerevisiae* AMF pre-pro sequence, a DNA sequence encoding AMF processing-site, lys-arg, a DNA operably encoding an EGF peptide in *P. pastoris* and a transcription terminator of a second *P. pastoris* gene, said first and second *P. pastoris* genes being identical or different, and the segments of said expression cassette being in operational association.

The DNA fragment according to the invention can be transformed into the *P. pastoris* cells as a linear fragment flanked by DNA sequences having sufficient homology with a target gene to effect integration of said DNA fragment therein. In this case integration takes place by replacement at the site of the target gene. Alternatively, the DNA fragment can be part of a circular plasmid, which may be linearized to facilitate integration, and will integrate by addition at a site of homology between the host and the plasmid sequence.

The invention further concerns an expression vector containing at least one copy of an expression cassette described hereinabove.

According to still further embodiment, the invention relates to a process for producing EGF peptides by growing *P. pastoris* transformants containing in their genome at least one copy of a DNA sequence operably encoding an EGF peptide in *P. pastoris*, operably associated with DNA encoding the *S. cerevisiae* AMF pre-pro sequence, both under the regulation of a promoter region of a *P. pastoris* gene, under conditions allowing the expression of said DNA sequence in said *P. pastoris* transformants and secreting mature EGF peptides into the culture medium. Cultures of viable *P. pastoris* cells capable of producing EGF peptides in *P. pastoris* are also within the scope of the invention.

The polypeptide product is secreted to the culture medium at surprisingly high concentrations. In our hands, the level of EGF peptides secretion is about two orders of magnitude higher than the best results published in the literature. In addition to the unique properties of the *P. astoris* expression system, these present, excellent results are also due to the fact that the *S. cerevisiae* alpha-mating factor pre-pro sequence functions unexpectedly well in *P. pastoris*.

Another surprising discovery is that the full length, 1-52 form of hEGF secreted by *P. pastoris* cells is not stable in the broth; it gets degraded to a shorter 1-48 amino acid containing, stable form. The shorter hEGF form has essentially the same biological activity as the full length hEGF.

It is contemplated herein that the use of the alpha-mating factor pre-pro sequence shall find broad applicability for successful secretion of a wider variety of appropriate heterologous polypeptides in mature form. As such, the description herein relating to the successful secretion of mature EGF using the alpha-mating factor pre-pro sequence is described as a preferred embodiment (best mode), and as such, serves as model from which may be borrowed details for the construction of operative expression vectors for use in the secreted expression of such additional heterologous polypeptide species.

Once having successfully reproduced the present invention in respect of mature EGF secretion via recombinant use of the alpha-mating factor pre-pro sequence, as described herein, one skilled in the art will well enough be enabled to construct appropriate, equivalent expression vectors, based upon this model system, for testing for successful secreted expression of such other heterologous polypeptides. Examples of such other heterologous polypeptides include invertase and alpha-mating factor and the appropriate DNA encoding such is described in the literature extant or is obtainable for tailoring and recombination via procedures known and documented by the art in the relevant time frame, in accord with present teachings.

The present invention is directed to the above aspects and all associated methods and means for accomplishing such. For example, the invention includes the technology requisite to suitable growth of the *P. pastoris* host cells, fermentation, and isolation and purification of the EGF gene product.

*P. pastoris* is described as a model system of the covered use of a methylotrophic yeast host, primarily due to its unique expression characteristics. Other useful methylotrophic yeasts can be taken from four genera, namely Candida, Hanensula, Pichia and Torulopsis. Equivalent species from them may be used as hosts herein primarily based upon their demonstrated characterization of being supportable for growth and exploitation on methanol as a single carbon nutriment source. See, for example, Gleeson et al., Yeast 4, 1 (1988).

BRIEF DESCRIPTION OF THE DRAWINGS

FIG. 1 shows the restriction map and insert sequence of plasmid pKK233-2 containing the hEGF gene (plasmid OMPFAEGF2).

A. Cell growth and EGF production for multicopy strain G-EGF817S9 (Run 425) and double copy strain G-EGF817S10 (Run 426) during methanol feed.

B. Cell growth and EGF production for multicopy strain G-EGF81759 (Run 419) and double copy strain G-EGF817S10 (Run 413) during mixed feed.

C. Comparison of multicopy strain in methanol feed (Run 425) and mixed feed (Run 426).

Figure 11:
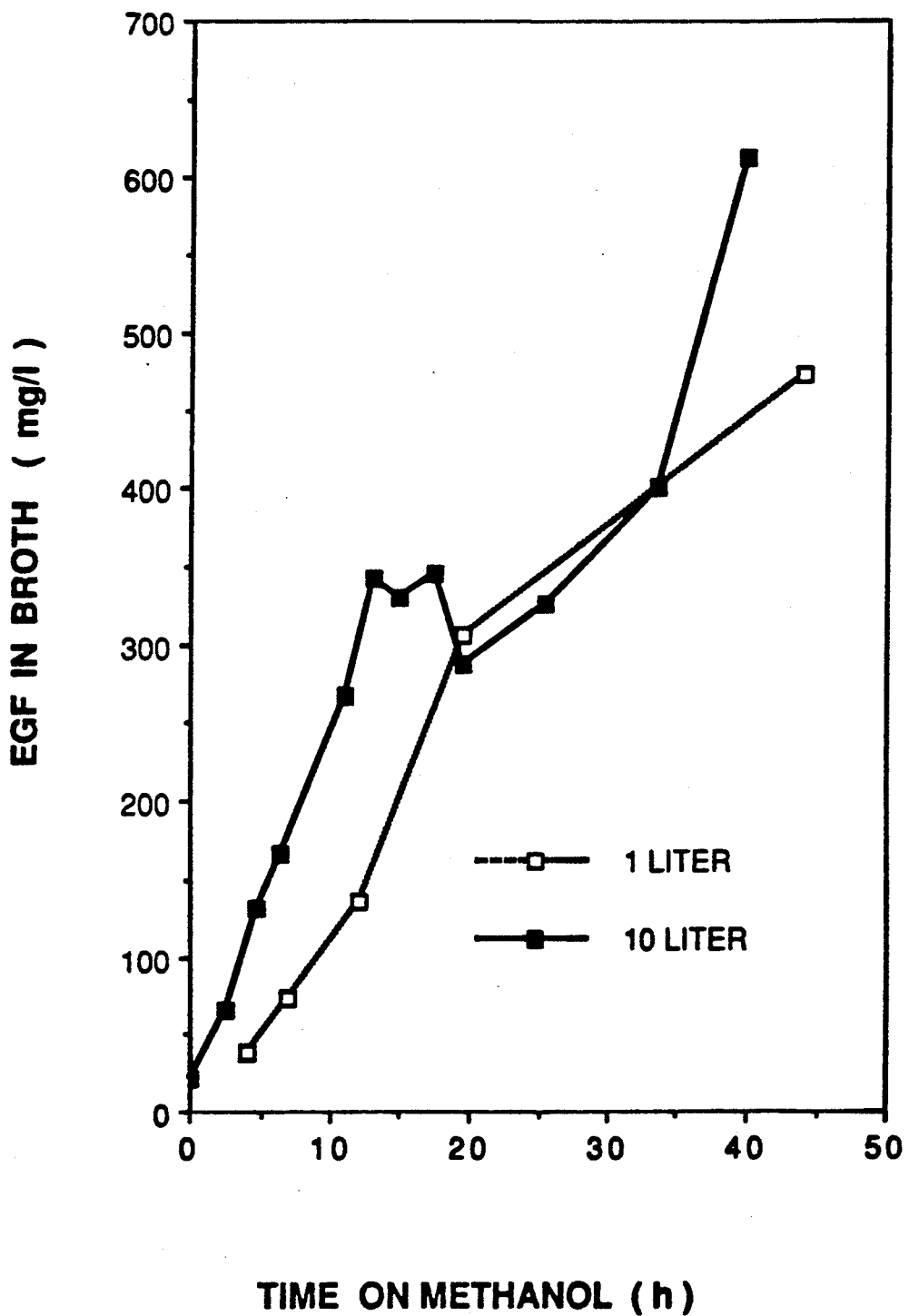

FIG. 11 shows the time course of hEGF production at both 1L and 10L volumes, employing Mut+ strain G+EGF819S4.

Figure 12:
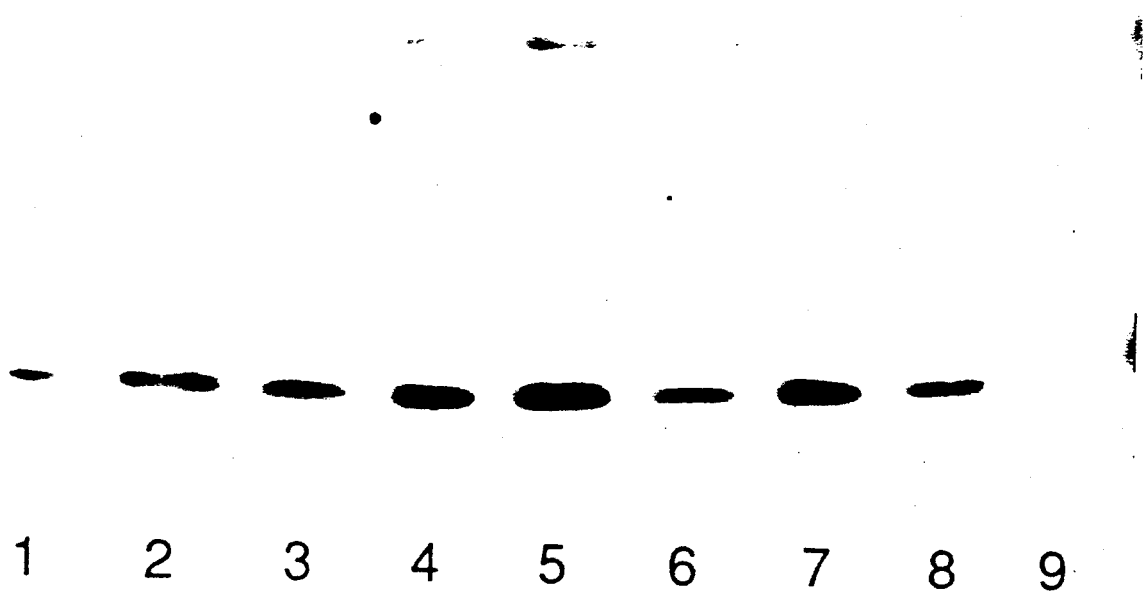

FIG. 12 is a Western blot of broth samples from six fermentor runs. Two μl aliquots of broth diluted in buffer were loaded on each lane after boiling in Laemmli buffer. Lane 1: 200 ng EGF std, Lane 2: 400 ng EGF std, Lane 3: Run 413 double copy, mixed-feed. Lane 4: Run 419 multi-copy, mixed-feed. Lane 5: Run 422 multicopy, mixed feed. Lane 6: Run 423 double copy, mixed feed. Lane 7: Run 425 multicopy, methanol feed. Lane 8: Run 426 double copy, methanol feed. Lane 9: Prestained markers.

Figure 13:
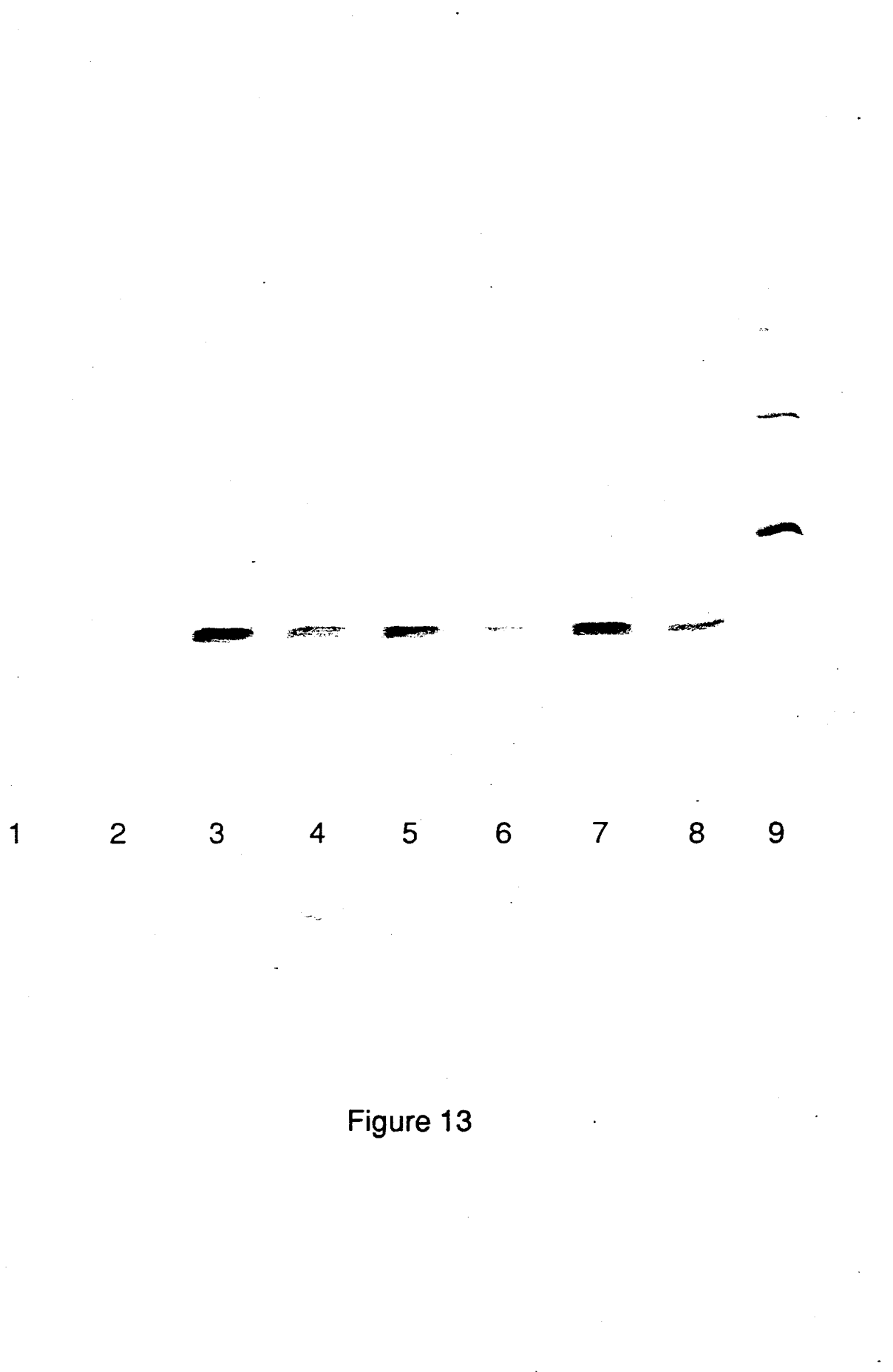

FIG. 13 shows a stained gel of the same samples as FIG. 12.

Figure 14:
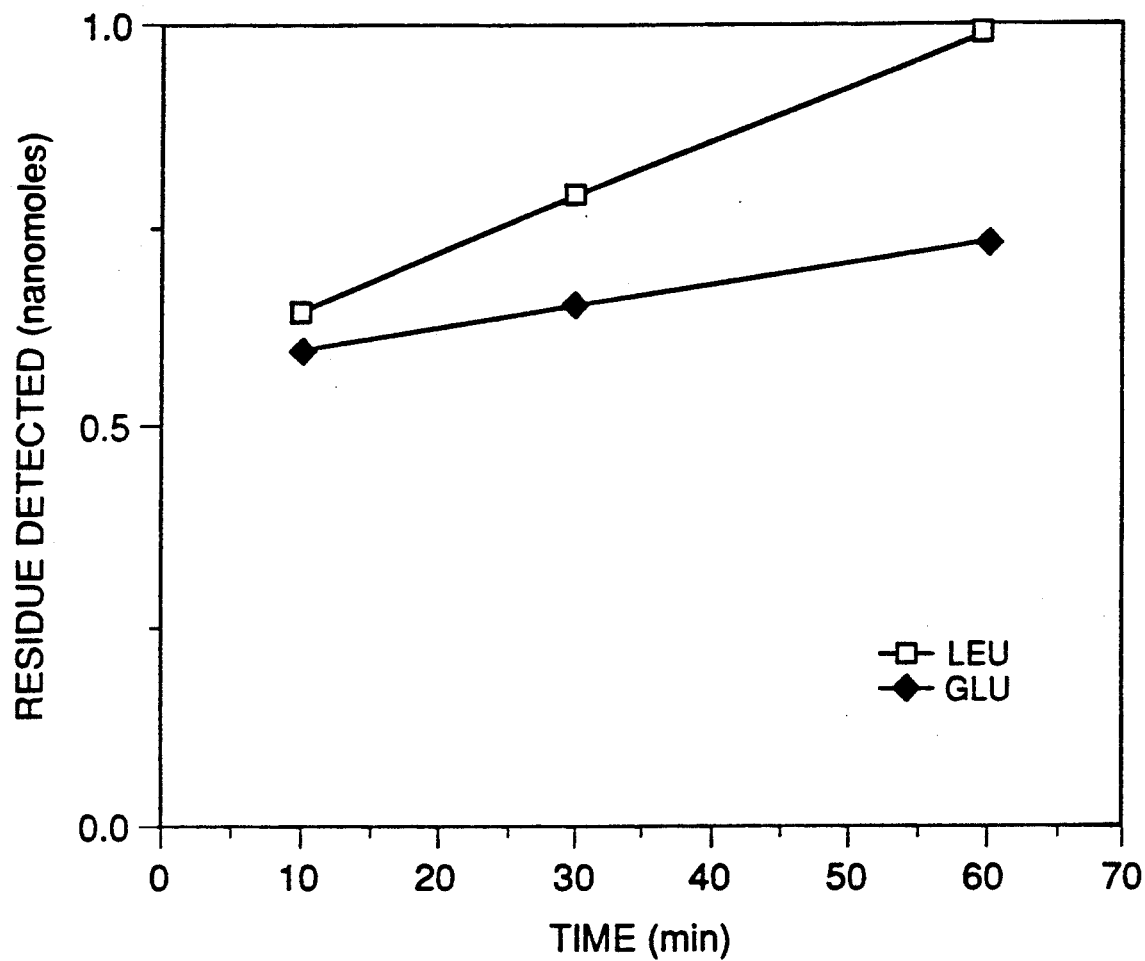

FIG. 14 shows carboxypeptidase digestion of hEGF over time.

Figure 15:
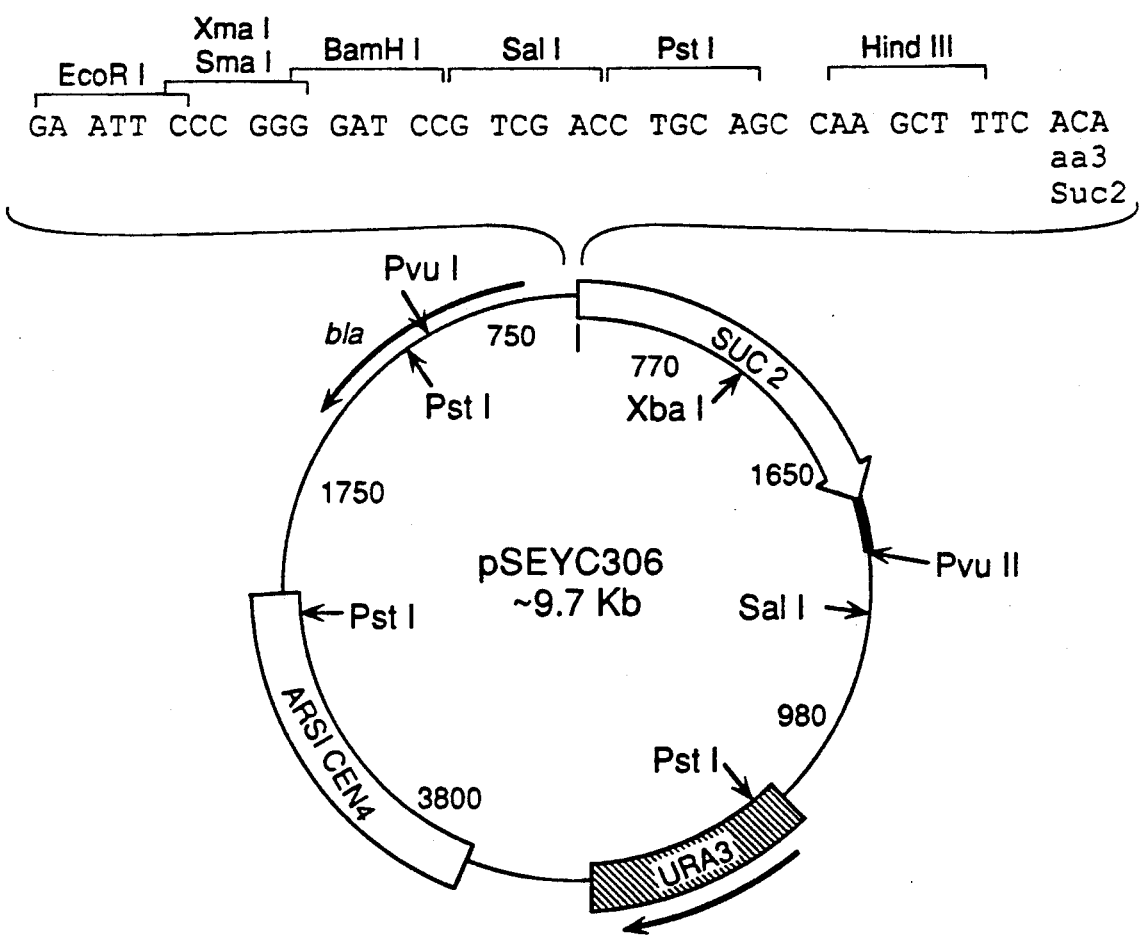

FIG. 15 shows the restriction map of plasmid pSEYC306.

FIG. 16 is the restriction map of plasmid pSAMSU1.

Figure 17:
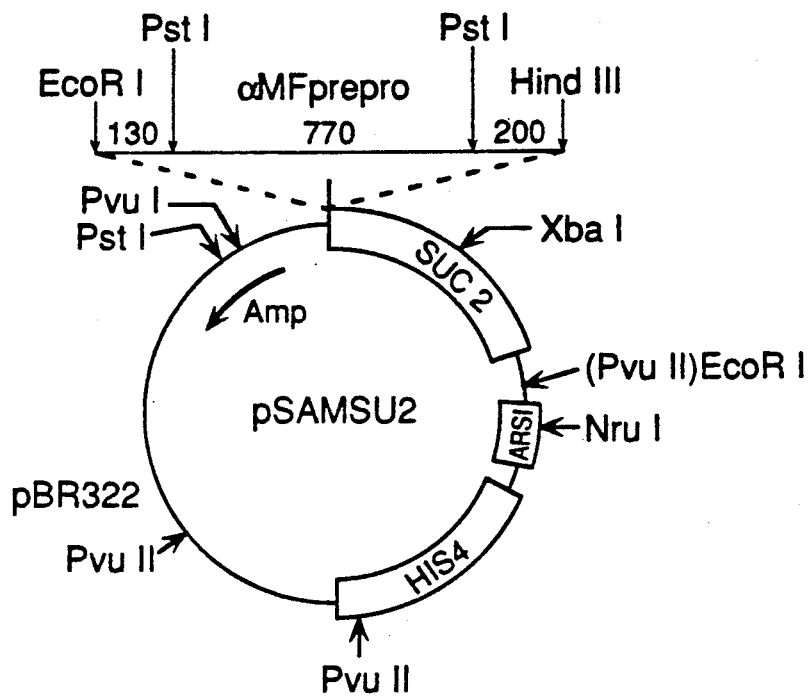

FIG. 17 depicts the restriction map of plasmid pSAMSU2.

DETAILED DESCRIPTION OF THE INVENTION

1. Definitions and General Methods

An expression system suitable for the production of EGF is provided.

The term "epidermal growth factor" or "EGF peptide", as used throughout the specification and in the claims, refers to a polypeptide product which exhibits similar, in-kind, biological activities to natural human epidermal growth factor (hEGF), as measured in recognized bioassays, and has substantially the same amino acid sequence as hEGF, including the 53, 52 and 48 amino acid forms. It will be understood that polypeptides deficient in one or more amino acids in the amino acid sequence reported in the literature for naturally occurring hEGF, or polypeptides containing additional amino acids or polypeptides in which one or more amino acids in the amino acid sequence of natural hEGF are replaced by other amino acids are within the scope of the invention, provided that they exhibit the functional activity of hEGF, e.g., inhibition of the secretion of gastric acid and promotion of cell growth. The invention is intended to embrace all the allelic variations of hEGF. Moreover, as noted Supra, derivatives obtained by simple modification of the amino acid sequence of the naturally occurring product, e.g, by way of site-directed mutagenesis or other standard procedures are included within the scope of the present invention. EGF forms produced by proteolysis of host cells that exhibit similar biological activities to mature, naturally occurring hEGF are also encompassed by the present invention.

The amino acids, which occur in the various amino acid sequences referred to in the specification have their usual, three- and one-letter abbreviations, routinely used in the art, i.e.:

| Amino Acid | Abbreviation | |
|---|---|---|
| L-Alanine | Ala | A |
| L-Arginine | Arg | R |
| L-Asparagine | Asn | N |
| L-Aspartic acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

According to the invention, EGF peptides are produced by *P. pastoris* yeast cells containing in their genome at least one copy of a DNA sequence operably encoding EGF peptides in *P. pastoris* operably associated with DNA encoding the *S. cerevisiae* α-mating factor (AMF) pre-pro sequence, both under the regulation of a promoter region of a *P. pastoris* gene.

The term "a DNA sequence operably encoding EGF peptides in *P. pastoris*" as used herein includes DNA sequences encoding the 53, 52 and 48 amino acid forms of hEGF or any other "EGF peptide" as defined herein above. DNA sequences encoding EGF, e.g. hEGF, are known in the art. They may be obtained by chemical synthesis or by transcription of a messenger RNA (mRNA) corresponding to EGF to a complementary DNA (cDNA) and converting the latter into a double stranded cDNA. The mRNA can be isolated for example, from adult mouse kidney [Rall et al., *Nature*. 313, 228 (1985)] or from adult human kidney (Bell et al., *Nucleic Acid Research*, 14, 21, 8427 (1986)]. Chemical synthesis of a gene for human EGF is, for example, disclosed by Urdea et al., Supra. The requisite DNA sequence can also be removed, for example, by restriction enzyme digest of known vectors harboring the EGF gene. Examples of such vectors and the means for their preparation can be taken from the following publications: Brake et al., Supra—e.g. the pBR322-based vector $pY_\alpha$ EGF-21; Urdea et al., Supra—plasmid pYEGF-2, etc. The structure of a preferred hEGF gene used in accordance with the present invention is further elucidated in the examples.

The promoter region employed to drive the EGF gene expression is derived from a methanol-regulated alcohol oxidase gene of *P. pastoris*. *P. pastoris* is known to contain two functional alcohol oxidase genes: alcohol oxidase I (AOX1) and alcohol oxidase II (AOX2) genes. The coding portions of the two AOX genes are closely homologous at the DNA and predicted amino acid sequence levels and share common restriction sites. The proteins expressed from the two genes have similar enzymatic properties but the promoter of the AOX1 gene is more efficient and highly expressed, therefore, its use is preferred for EGF expression. The AOX1 gene, including its promoter, has been isolated and thoroughly characterized [Ellis et al., *Mol. Cell. Biol.* 5, 1111 (1985)].

The expression cassette used for transforming *P. pastoris* cells contains, in addition to the *P. pastoris* promoter and the EGF encoding DNA sequence (EGF gene) DNA encoding the in-reading frame *S. cerevisiae* AMF pre-pro sequence, a DNA sequence encoding AMF processing site, lys-arg (also referred to as lys-arg encoding sequence) and a *P. pastoris* transcription terminator.

Figure 3:
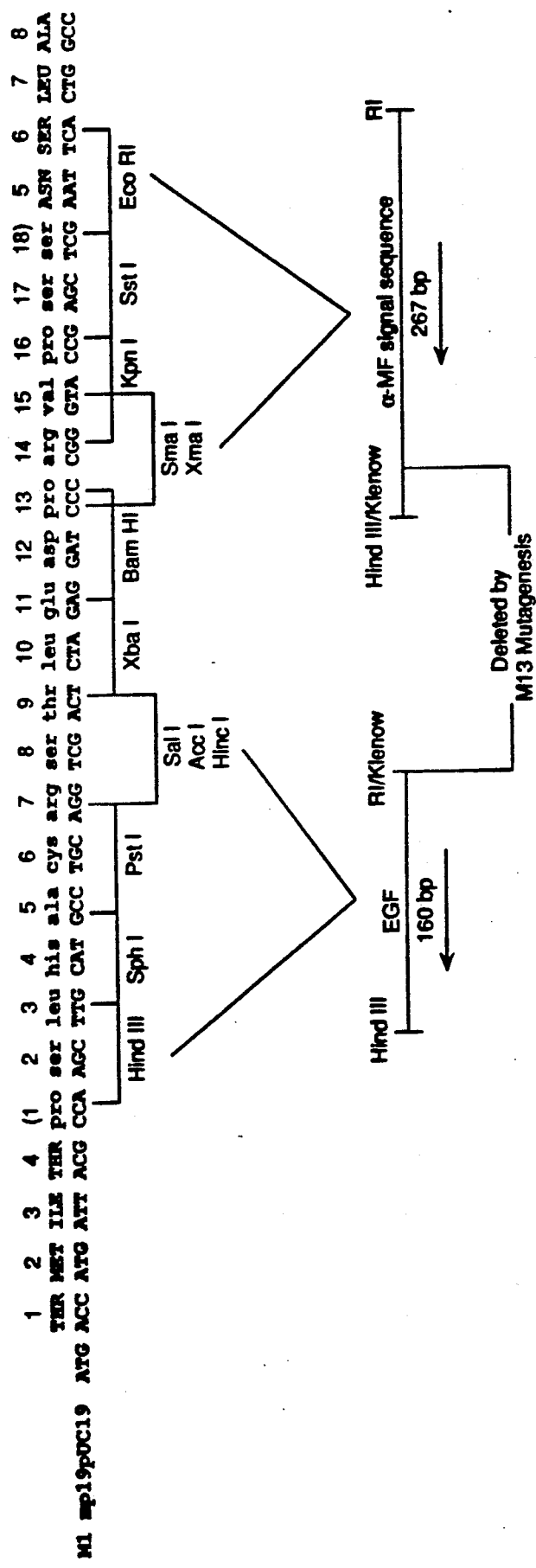
FIG. 3 illustrates the insertion of the hEGF gene and AMF pre-pro sequence into M13mp19.

The *S. cerevisiae* alpha-mating factor is a 13-residue peptide, secreted by cells of the "alpha" mating type, that acts on cells of the opposite "a" mating type to promote efficient conjugation between the two cell types and thereby formation of "a-alpha" diploid cells [Thorner et al., *The Molecular Biology the Yeast Saccharomyces*, Cold Spring Harbor Laboratory, Cold Spring Harbor, N.Y., 143 (1981)]. The AMF pre-pro sequence is a leader sequence contained in the AMF precursor molecule, which, together with the lys-arg encoding sequence is necessary for proteolytic processing and secretion (see e.g. Brake et al., Supra). The AMF pre-pro sequence, including the lys-arg encoding sequence is a 255 bp fragment which is illustrated in FIG. 3.

The *P. pastoris* transcription terminator used in accordance with the present invention has a subsegment which encodes a polyadenylation signal and polyadenylation site in the transcript and/or a subsegment which provides a transcription termination signal for transcription from the promoter used in the expression cassette according to the invention (the term "expression cassette" as used herein and throughout the specification and claims refers to a DNA sequence which includes sequences functional for expression and the secretion processes). The entire transcription terminator is taken from a *P. pastoris* protein-encoding gene, which may be the same or different from the *P. pastoris* gene which is the source of the *P. pastoris* promoter used according to the invention.

For the practice of the present invention it is preferred that six of the above-described expression cassettes be contained on one DNA fragment in a head-to-tail orientation.

The DNA fragments according to the invention further comprise a selectable marker gene. For this purpose, any selectable marker gene functional in *P. pastoris* may be employed, i.e., any gene which confers a phenotype upon *P. pastoris* cells thereby allowing them to be identified and selectively grown from among a vast majority of untransformed cells. Suitable selectable marker genes include, for example, selectable marker systems composed of an auxotrophic mutant *P. pastoris* host strain and a wild type biosynthetic gene which complements the host's defect. For transformation of his4− *P. pastoris* strains, for example, the *S. cerevisiae* or *P. pastoris* HIS4 gene, or for transformation of arg4− mutants the *S. cerevisiae* ARG4 gene or the *P. pastoris* ARG4 gene, may be employed.

If the yeast host is transformed with a linear DNA fragment containing the EGF gene under the regulation of a promoter region of a *P. pastoris* gene and sequences necessary for processing and secretion, the expression cassette is integrated into the host genome by any of the gene replacement techniques known in the art, such as by one-step gene replacement [see e.g., Rothstein, *Methods Enzymol.* 101, 202 (1983); Cregg et al., *Bio/Technology* 5, 479 (1987)] or by two-step gene replacement methods [see e.g., Scherer and Davis, *Proc. Natl. Acad. Sci. USA*, 76, 4951 (1979)]. The linear DNA fragment is directed to the desired locus, i.e., to the target gene to be disrupted by means of flanking DNA sequences having sufficient homology with the target gene to effect integration of the DNA fragment therein. One-step gene disruptions are usually successful if the DNA to be introduced has as little as 0.2 kb homology with the fragment locus of the target gene; it is however, preferable to maximize the degree of homology for efficiency.

If the DNA fragment according to the invention is contained within or is an expression vector, e.g., a circular plasmid, one or more copies of the plasmid can be integrated at the same or different loci, by addition. Linearization of the plasmid by means of a suitable restriction endonuclease facilitates integration.

The term "expression vector" includes vectors capable of expressing DNA sequences contained therein, where such sequences are in operational association with other sequences capable of effecting their expression, i.e. promoter sequences. In general, expression vectors usually used in recombinant DNA technology are often in the form of "plasmids", i.e. circular, double-stranded DNA loops which in their vector form, are not bound to the chromosome. In the present specification the terms "vector" and "plasmid" are used interchangeably. However, the invention is intended to include other forms of expression vectors as well, which function equivalently.

In the DNA fragment according to the invention the segments of the expression cassette are "in operational association". The DNA sequence encoding EGF peptides is positioned and oriented functionally with respect to the promoter, the DNA encoding the S. cerevisiae AMF pre-pro sequence, the DNA sequence encoding AMF processing-site, lys-arg and the transcription terminator, so that the polypeptide encoding segment is transcribed, under regulation of the promoter region, into a transcript capable of providing, upon translation the desired polypeptide in P. pastoris. Because of the presence of the AMF pre-pro sequence of the expressed product, EGF is found as a secreted entity in the culture medium. Appropriate reading frame positioning and orientation of the various segments of the expression cassette are within the knowledge of persons of ordinary skill in the art; further details are given in the Examples.

The DNA fragment provided by the present invention may include sequences allowing for its replication and selection in bacteria, especially E. coli. In this way, large quantities of the DNA fragment can be produced by replication in bacteria.

Methods of transforming Pichia pastoris as well as methods applicable for culturing P. pastoris cells containing in their genome a gene for a heterologous protein are known generally in the art.

According to the invention, the expression cassettes are transformed into the P. pastoris cells either by the spheroplast technique, described by Cregg et al., Mol. Cell. Biol. 5, 3376 (1985) or by the whole-cell lithium chloride yeast transformation system [Ito et al., Agric. Biol. Chem. 48, 341 (1984)], with minor modification necessary for adaptation to P. pastoris. Although the whole-cell lithium chloride method is more convenient in that it does not require the generation and maintenance of spheroplasts, for the purpose of the present invention the spheroplast method is preferred, primarily since it yields a greater number of transformants.

Positive transformants are characterized by Southern blot analysis [Maniatis et al., Molecular Cloning: A Laboratory Manual, Cold Spring Harbor Laboratory Press, Cold Spring Harbor, N.Y., U.S.A. (1982)] for the site of DNA integration, Northern blots [Maniatis, Op. Cit., R. S. Zitomer and B. D. Hall, J. Biol. Chem. 251, 6320 (1976)] for methanol-responsive EGF gene expression, and product analysis for the presence of secreted EGF peptides in the growth media.

Transformed strains, which are of the desired phenotype and genotype are grown in fermentors. For the large-scale production of recombinant DNA-based products in P. pastoris a three-stage, high cell-density, batch fermentation system is normally employed. In the first, or growth stage expression hosts are cultured in defined minimal medium with excess glycerol as carbon source. On this carbon source heterologous gene expression is completely repressed, which allows the generation of cell mass in the absence of heterologous protein expression. Next, a short period of glycerol limitation growth is allowed. Subsequent to the glycerol limited growth, methanol is added, initiating the expression of the desired heterologous protein. This third stage is the so-called production stage.

The term "culture" means a propagation of cells in a medium conductive to their growth, and all sub-cultures thereof. The term "subculture" refers to a culture of cells grown from cells of another culture (source culture), or any subculture of the source culture, regardless of the number of subculturings which have been performed between the subculture of interest and the source culture.

2. Description of the Preferred Embodiment

According to a preferred embodiment of the invention, the heterologous protein expression system used for EGF production utilizes the promoter derived from the methanol-regulated AOX1 gene of P. pastoris, which is very efficiently expressed and tightly regulated. This gene is the source of the transcription terminator as well. The expression cassette comprises, in operational association, a P. pastoris AOX1 promoter, DNA encoding the S. cerevisiae AMF pre-pro sequence, a DNA sequence encoding AMF processing site, lys-arg, a DNA sequence encoding mature hEGF and a transcription terminator derived from the P. pastoris AOX1 gene. Preferably, two or more of such expression cassettes are contained on one DNA fragment, in head-to-tail orientation to yield an expression cassette tandem.

The host cells to be transformed with the expression cassette tandem are P. pastoris cells having at least one mutation that can be complemented with a marker gene present on a transforming DNA fragment. Preferably his4− (GS115) or arg4− (GS190) auxotrophic mutant P. pastoris strains are employed.

The expression cassette tandem is inserted into a plasmid containing a marker gene complementing the host's defect. pBR322-based plasmids, e.g. pAO815 are preferred. Plasmid pAO815 comprising tandem hEGF expression/secretion cassettes is called pAO817 and pEGF819.

To develop Mut− expression strains, the expression cassette tandem is preferably integrated into the host genome after digesting the expression vector with an appropriate enzyme yielding a linear DNA fragment with ends homologous to the AOX1 locus by means of the flanking homologous sequences, and the expression cassette tandem is integrated into the host genome by a one-step gene replacement technique. This approach avoids the problems encountered with S. cerevisiae promoters, which must be present on multicopy plasmids to achieve high level of expression. As a result of gene replacement Mut− strains are obtained. Mut refers to the methanol-utilization phenotype. In Mut− strains, the AOX1 gene is replaced with the expression cassette, thus decreasing its ability to utilize methanol. A slow growth rate on methanol is maintained by expression of the AOX2 gene product. The transformants in which the expression cassette has integrated into the AOX1 locus by site-directed recombination can be identified by first screening for the presence of the complementing gene. This is preferably accomplished by growing the cells in a media lacking the complementing gene product and identifying those cells which are able to grow by nature of expression of the complementing gene. Next, the selected cells are screened for their Mut phenotype by growing them in the presence of methanol and monitoring their growth rate.

To develop Mut+ EGF-expressing strains, the expression cassette tandem preferably is integrated into the host genome by transformation of the host with a circular plasmid comprised of the tandem. The integration is by addition at a locus or loci having homology with one or more sequences present on the transformation vector.

Positive transformants are characterized by Southern analysis for the site of DNA integration, by Northern analysis for methanol-responsive EGF gene expression, and by product analysis for the presence of secreted hEGF peptides in the growth media. *P. pastoris* strains which have integrated one or multiple copies of the tandem expression cassettes at a desired site are identified by Southern blot analysis. Strains which demonstrate enhanced secretion of hEGF may be identified by Northern or product analysis; however, this characteristic is not always easy to detect in shake-flask experiments.

*P. pastoris* transformants which are identified to have the desired genotype and phenotype are grown in fermentors. Typically a three-step production process is used. Initially, cells are grown on a repressing carbon source, preferably excess glycerol. In this stage the cell mass is generated in absence of expression. Next, a short period of glycerol limitation growth is allowed. After exhaustion of glycerol, methanol alone (methanol excess fed-batch mode) or limiting glycerol and methanol (mixed-feed fed-batch mode) are added in the fermentor, resulting in the expression of the hEGF gene driven by the AOX1 promoter. The level of hEGF secreted into the media can be determined by Western blot analysis of the media in parallel with an EGF standard, using anti-EGF antisera, or by HPLC after suitable pretreatment of the medium.

The invention is further illustrated by the following non-limiting examples.

3. Examples

Example 1 a. Construction of the Expression Vector pA0817

The expression vector construction disclosed in the present application was performed using standard procedures, as described, for example in Maniatis et al., Supra, and Davis et al., *Basic Methods in Molecular Biology*, Elsevier Science Publishing, Inc., New York (1986).

The hEGF gene was received in plasmid pKK233-2 from Glaxo. The restriction map of the pBR322-based plasmid pKK233-2 containing the hEGF gene (plasmid OMPAEGF2) is shown in FIG. 1. 30 μg of plasmid OMPAEGF2 were digested with EcoRI, filled in with Klenow-fragment DNA polymerase, and digested with HindIII. The digestion was run on a 2% agarose gel and the 160 bp fragment comprised of the hEGF gene was isolated.

Figure 2:
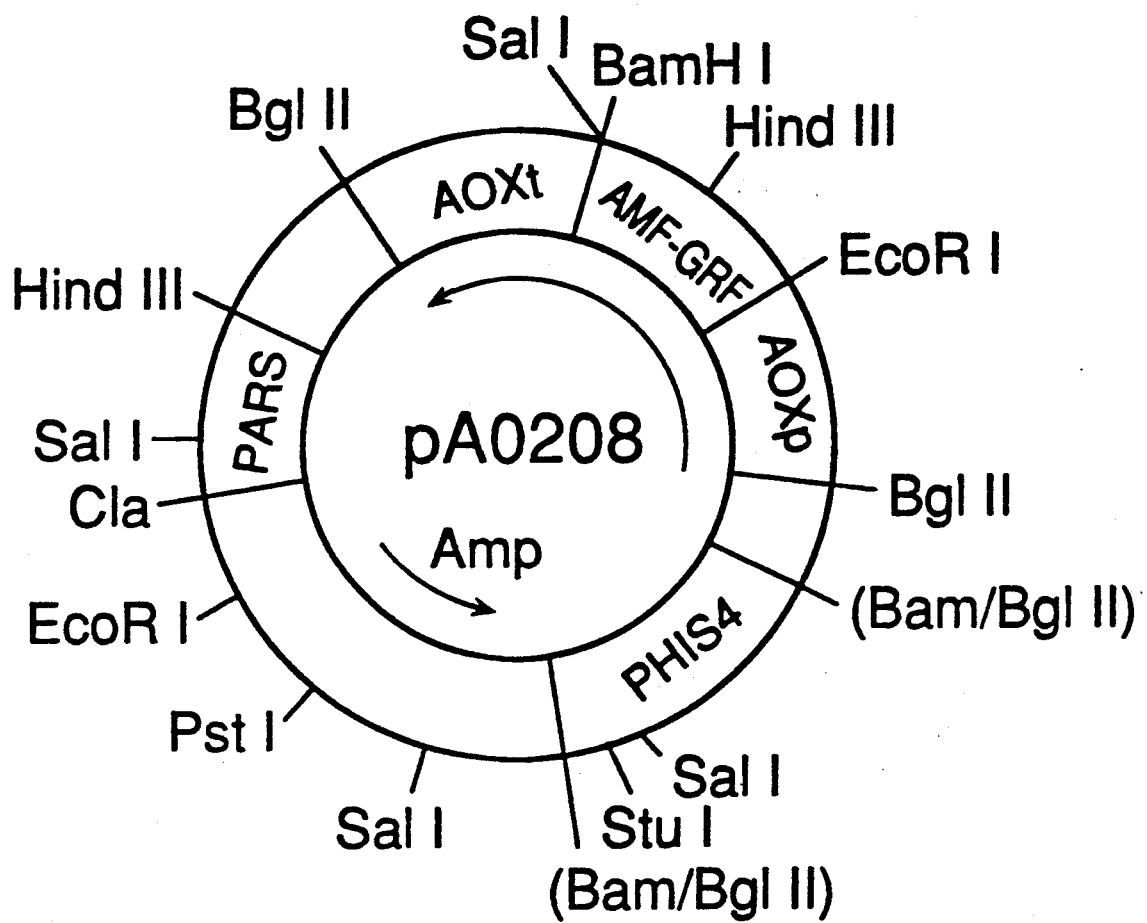
FIG. 2 is the restriction map of plasmid pA0208.

The AMF pre-pro sequence was isolated from plasmid pA0208, FIG. 2, the construction of which is described hereinafter. 15 μg of plasmid pA0208 were digested with HindIII, filled in with Klenow-fragment DNA polymerase, and digested with EcoRI. The digestion was run on a 1.7% agarose gel and the 267 bp fragment comprised of the AMF pre-pro sequence was isolated. The hEGF gene and the AMF pre-pro sequence in the same translational direction were inserted into M13mp19, [New England Biolabs] as illustrated in FIG. 3, by the following procedure:

10 μg of M13mp19 were digested with SmaI and EcoRI and the large, about 7240 bp plasmid fragment was isolated on a 0.8% agarose gel. The plasmid fragment and the 267 bp AMF fragment were ligated together by T4 DNA ligase. The ligation mixture was transformed into JM103 cells and DNA from the plaque was characterized. Plasmid DNA was prepared from these cells and was digested with SalI, filled in the Klenow-fragment DNA polymerase, and cut with HindIII. The about 7400 bp plasmid fragment was isolated and ligated to the 160 bp hEGF gene fragment. The ligation mixture was transformed into JM101 cells (that are widely available) and plaques were selected. Cells having the M13mp19 plasmid with both the EGF gene and the AMF pre-pro sequence in the same translational direction were called pEGF19-3.

In vitro mutagenesis was performed on pEGF19-3 to remove the polylinker of M13mp19 and to place the DNA sequence, encoding AMF processing site, lys-arg, directly in front of the first codon of mature EGF. The mutagenesis was accomplished using standard techniques [Zoller and Smith, *Meth. Enzymol.* 100, 468 (1983)]. The mutagenizing oligonucleotide employed was of the following sequence: 5' TTC TTT GGA TAA AAG AAA TTC CGA TAG CGA GT 3'. The screening oligonucleotide was of sequence: GATAAAAGAAATTCCGAT. The mutagenized plasmid was called pEGF19m-2.

Figure 4:
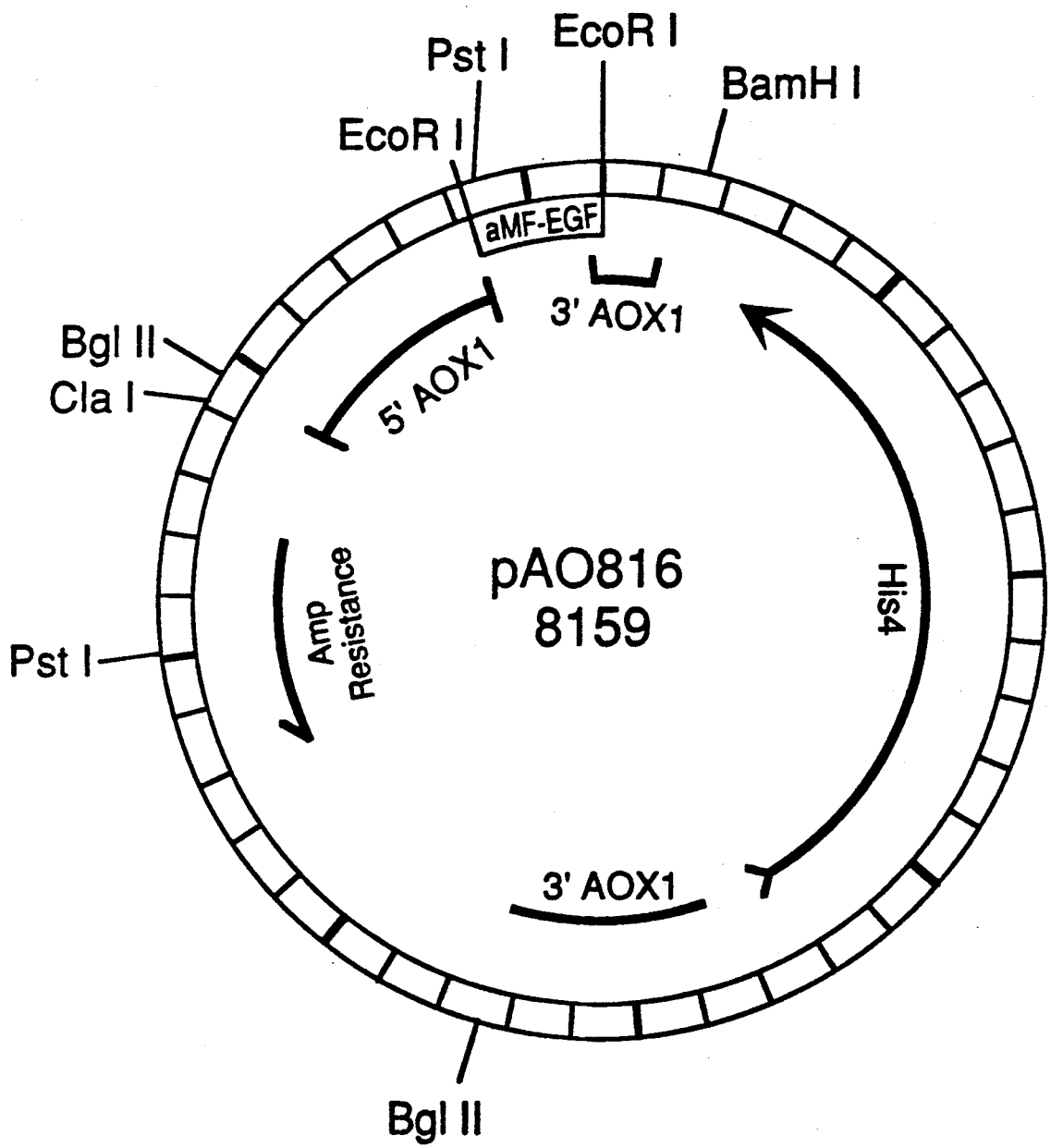
FIG. 4 is a restriction map of plasmid pA0816.

EcoRI linkers of sequence GGAATTCC were added to the 3' end of the hEGF gene in the plasmid pEGF19m-2 by first digesting 20 μg of the plasmid with HindIII and then filling in with Klenow-fragment DNA polymerase. 1 μg of linkers and 20 μg of treated plasmid were ligated together and then digested with EcoRI to remove excess linkers. The ≈435 bp EcoRI fragment was isolated on a 1.5% agarose gel. 15 μg of the plasmid pA0815 (the construction of which is described below) were digested with EcoRI and ligated to the 435 bp EcoRI fragment in a standard ligation reaction. The reaction was used to transform MC1061 cells (that are widely available) and amp$^r$ cells were selected. To determine which cells have a plasmid with the correct orientation of the AMF pre-pro sequence—hEGF gene insert, plasmid DNA was prepared from the amp$^r$ colonies and was digested with PstI. A correct construct yielded an about 1740 bp fragment. Colonies demonstrating the correct restriction pattern were called pA0816 (FIG. 4).

Figure 5:
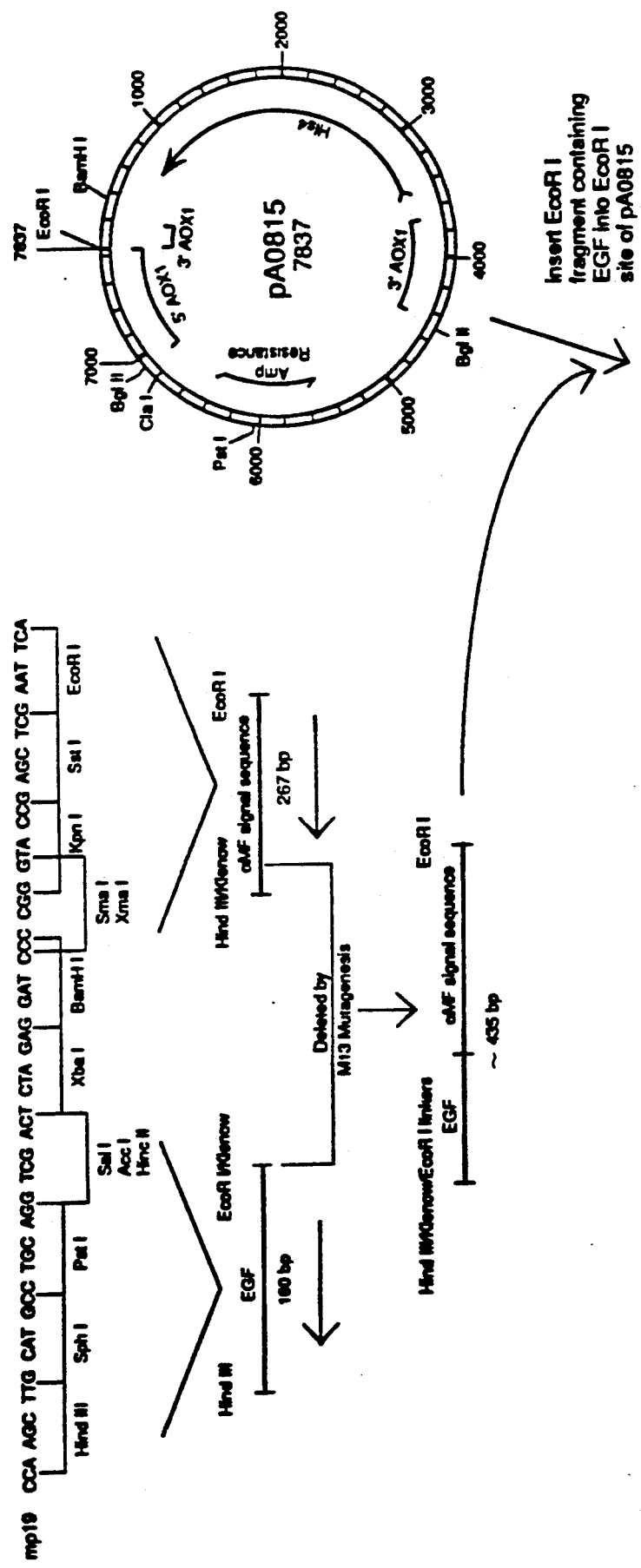
FIG. 5 depicts the construction of plasmid pA0817.
Figure 5:
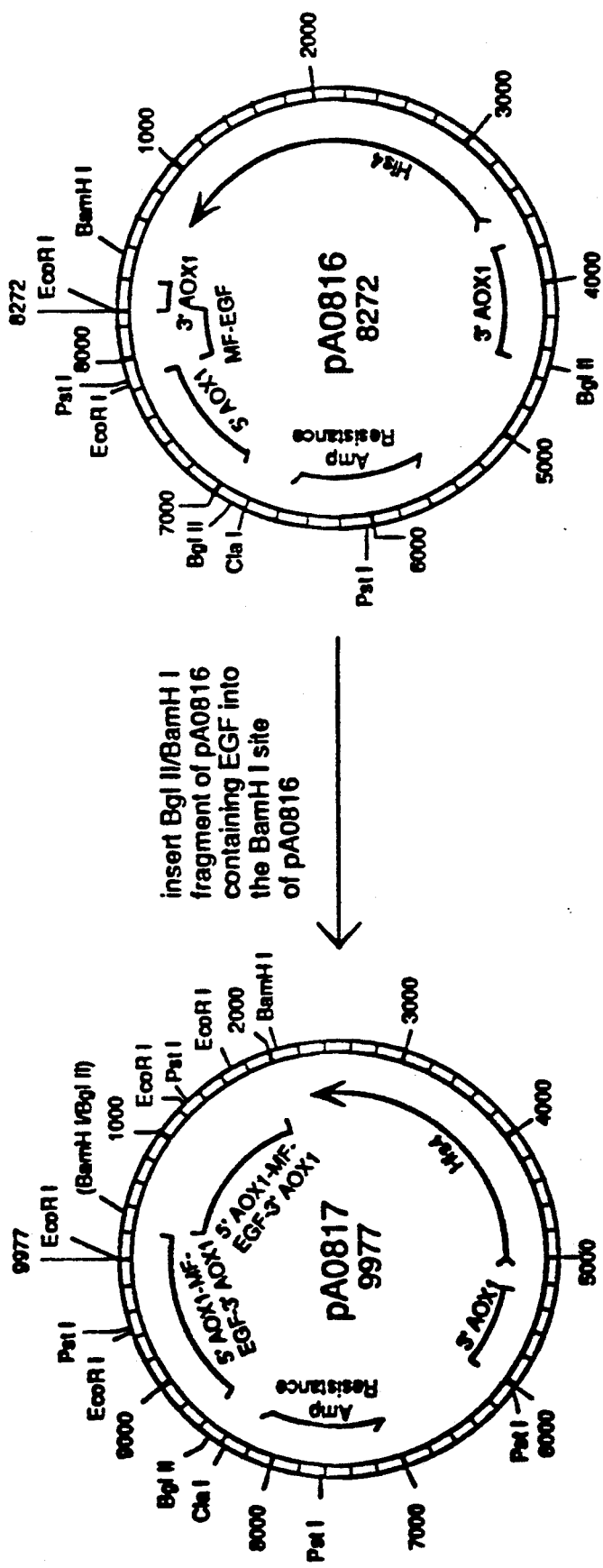
Figure 6:
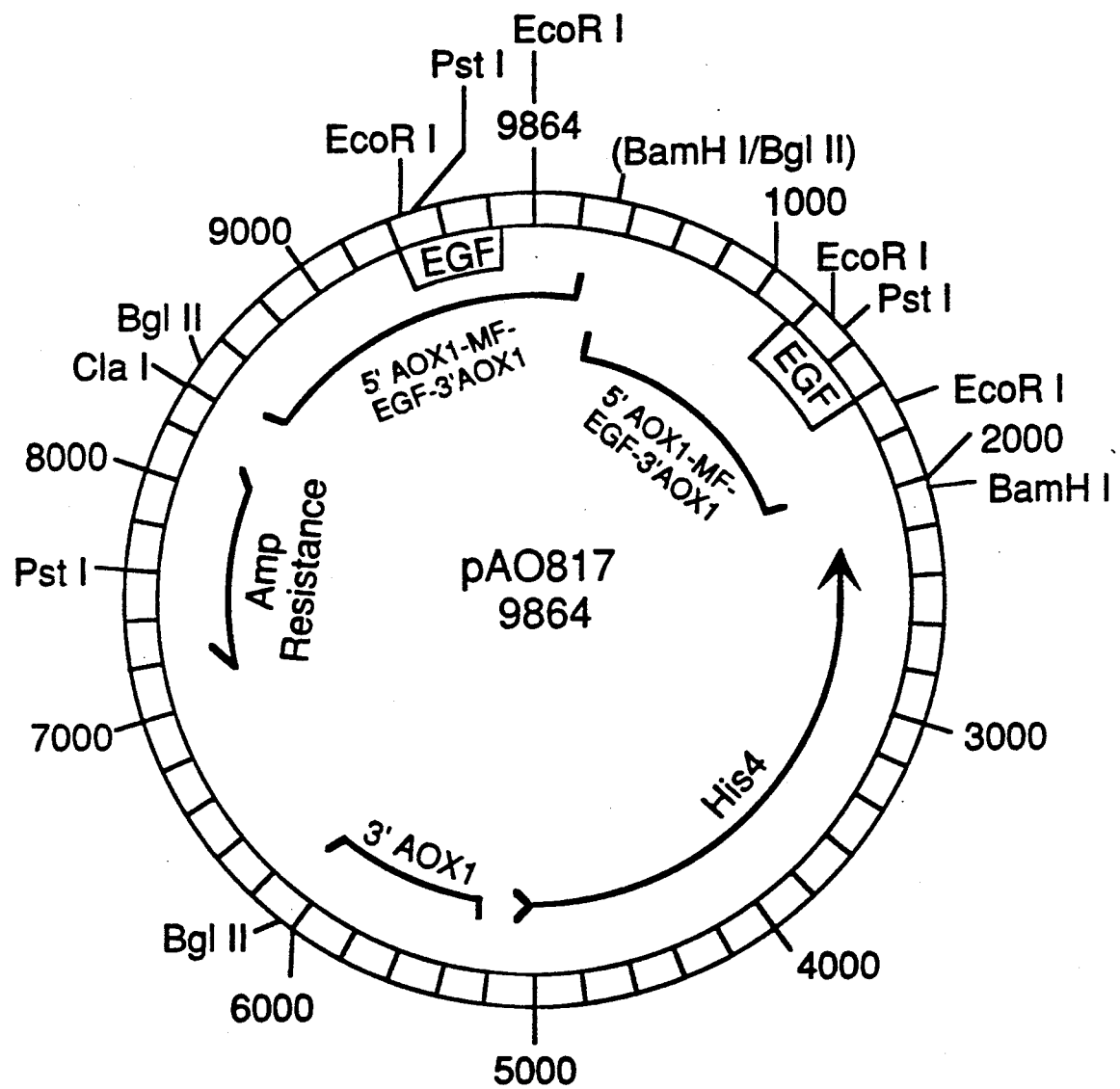
FIG. 6 is a restriction map of plasmid pA0817.

The complete, AOX1-promoter expression cassette was removed from pA0816 by digesting 15 μg of pA0816 with BglII and BamHI, and isolating the about 1670 bp fragment on a gel. The gel-purified fragment was then ligated to BamHI-cut pA0816. The ligation mix was used to transform MC1061 cells and amp$^R$ colonies were selected. Colonies having plasmids comprised of two head-to-tail expression cassettes were identified by digestion with PstI, which gave fragments of 1827, 1497 and 9547 bp. These plasmids were called pA0817. The construction procedure is shown in FIG. 5; the restriction map of pA0817 in FIG. 6.

b. Construction of Plasmid pA0208

Figure 7:
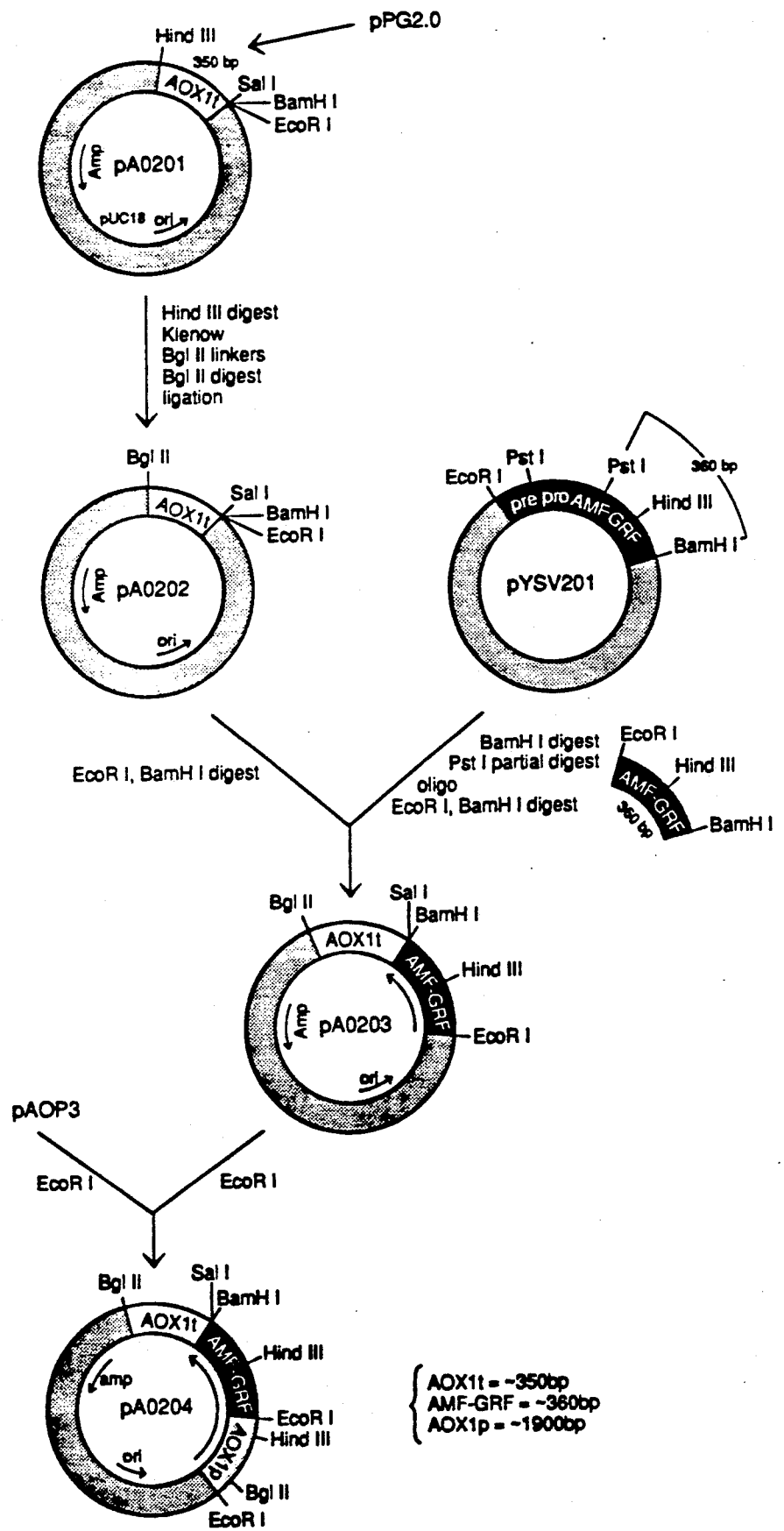
FIG. 7 depicts the construction of plasmid pA0208.
Figure 7:
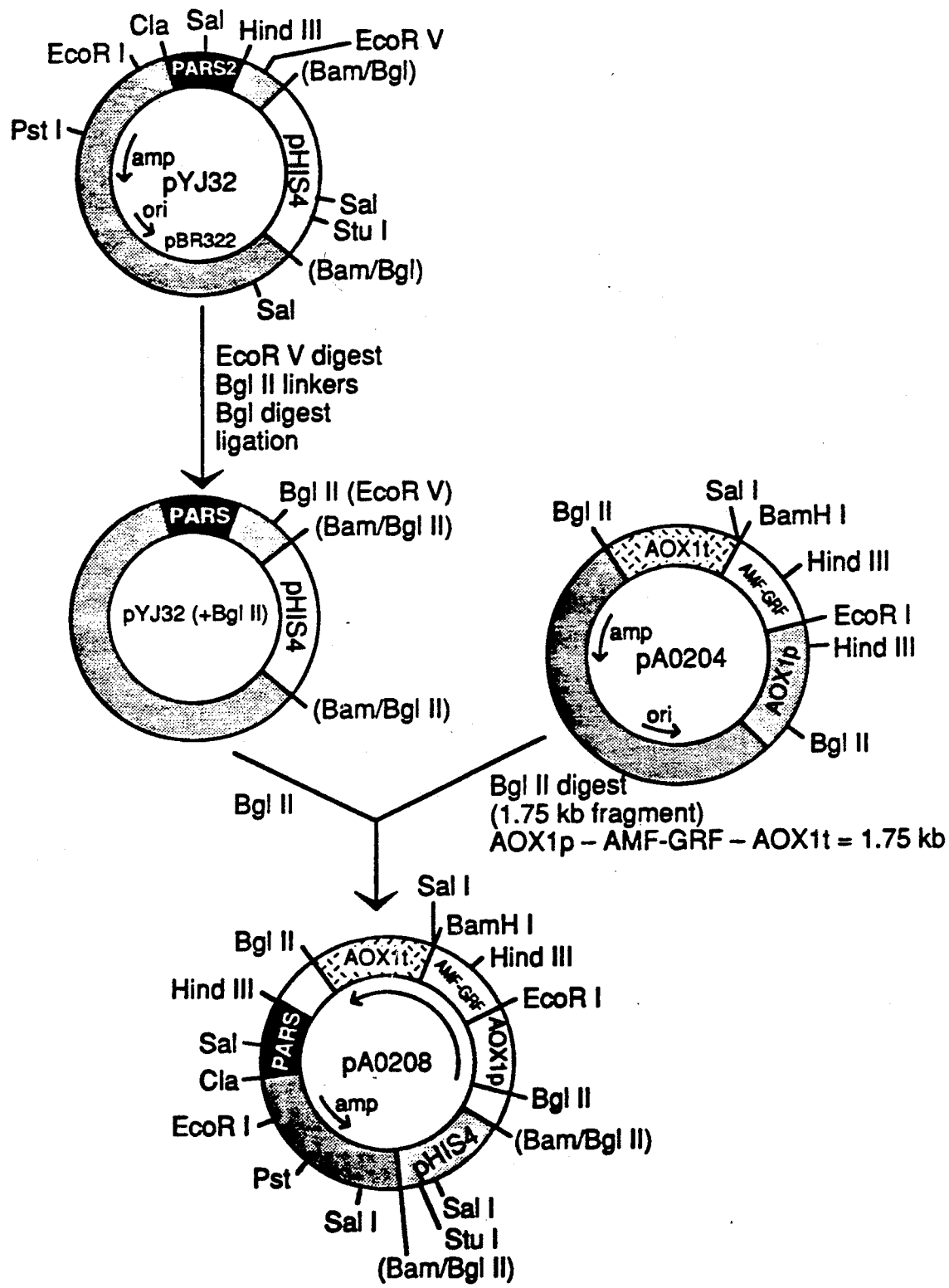

Many of the plasmids described in this section are shown in FIG. 7. The AOX1 transcription terminator was isolated from 20 μg of ppg2.0 [ppg2.0=BamHI-HindIII fragment of pG4.0 (NRRL 15868)+pBR322] by StuI digestion followed by the addition of 0.2 μg SalI linkers (GGTCGACC). The plasmid was subsequently digested with HindIII and the 350 bp fragment isolated from a 10% acrylamide gel and subcloned into pUC18 (Boehringer Mannheim) digested with HindIII and SalI. The ligation mix was transformed into JM103 cells (that are widely available) and amp$^R$ colonies were selected. The correct construction was verified by HindIII and SalI digestion, which yielded a 350 bp fragment, and was called pAO201.

5 μg of pAO201 was digested with HindIII, filled in using Klenow polymerase, and 0.1 μg of BglII linkers (GAGATCTC) were added. After digestion of the excess BglII linkers, the plasmid was reclosed and transformed into MC1061 cells. Amp$^R$ cells were selected, DNA was prepared, and the correct plasmid was verified by BglII, SalI double digests, yielding a 350 bp fragment, and by a HindIII digest to show loss of HindIII site. This plasmid was called pAO202.

The alpha factor-GRF fusion was isolated as a 360 bp BamHI-PstI partial digest from pYSV201. Plasmid pYSV201 is the EcoRI-BamHI fragment of GRF-E-3 inserted into M13mp18 (New England Biolabs). Plasmid GRF-E-3 is described in EP 206,783. 20 μg of pYSV201 plasmid was digested with BamHI and partially digested with PstI. To this partial digest was added the following oligonucleotides:

5' AATTCGATGAGATTTCCTTCAATTTTTACTGCA 3'
3'     GCTACTCTAAAGGAAGTTAAAAATG 5'.

Only the antisense strand of the oligonucleotide was kinase labelled so that the oligonucleotides did not polymerize at the 5'- end. After acrylamide gel electrophoresis (10%), the fragment of 385 bp was isolated by electroelution. This EcoRI-BamHI fragment of 385 bp was cloned into pAO202 which had been cut with EcoRI and BamHI. Routinely, 5 ng of vector cut with the appropriate enzymes and treated with calf intestine alkaline phosphatase, was ligated with 50 ng of the insert fragment. MC1061 cells were transformed, amp$^r$ cells were selected, and DNA was prepared. In this case, the resulting plasmid, pAO203, was cut with EcoRI and BglII to yield a fragment of greater than 700 bp. The α-factor-GRF fragment codes for the (1-40)leu$^{27}$ version of GRF and contains the processing sites lys-arg-glu-ala-glu-ala.

The AOX1 promoter was isolated as a 1900 bp EcoRI fragment from 20 μg of pAOP3 and subcloned into EcoRI-digested pAO203. The development of pAOP3 is disclosed in EP 226,846 and described hereinbelow. MC1061 cells were transformed with the ligation reaction, amp$^r$ colonies were selected, and DNA was prepared. The correct orientation contains a ≈376 bp HindIII fragment, whereas the wrong orientation has an ≈675 bp fragment. One such transformant was isolated and was called pAO204.

The parent vector for pAO208 is the HIS4, PARS2 plasmid pYJ32 (NRRL B-15891) which was modified to change the EcoRV site in the tet$^R$ gene to a BglII site, by digesting PYJ32 with EcoRV and adding BglII linkers to create pYJ32(+BglII). This plasmid was digested with BglII and the 1.75 Kb BglII fragment from pAO204 containing the AOX1 promoter-α factor GRF-AOX1 3' expression cassette was inserted. The resulting vector was called pAO208. For no real reason, the orientation shown in FIG. 7 was chosen. This orientation was verified by an EcoRI digest yielding an 850 bp fragment+vector, as opposed to 1.1 Kb+vector in the other orientation.

c. Construction of Plasmid pAOP3

1. Plasmid ppg2.5 [a pBR322 based plasmid containing the approximately 2.5 Kbp EcoRI-SalI fragment from plasmid ppg4.0, which plasmid contains the primary alcohol oxidase gene (AOX1) and regulatory regions and which is available in an *E. coli* host from the Northern Regional Research Center of the United States Department of Agriculture in Peoria, Ill. as NRRL B-15868] was linearized with BamHI.

2. The linearized plasmid was digested with BAL31;

3. The resulting DNA was treated with Klenow fragment to enhance blunt ends, and ligated to EcoRI linkers;

4. The ligation products were transformed into *E. coli* strain MM294;

5. Transformants were screened by the colony hybridization technique using a synthetic oligonucleotide having the following sequence:

5'TTATTCGAAACGGGAATTCC.

This oligonucleotide contains the AOX1 promoter sequence up to, but not including, the ATG initiation codon, fused to the sequence of the EcoRI linker;

6. Positive clones were sequenced by the Maxam-Gilbert technique. All three positives had the following sequence:

5'... TTATTCGAAACGAGGAATTCC ... 3'.

They all retained the "A" of the ATG (underlined in the above sequence). It was decided that this A would probably not be detrimental; thus all subsequent clones are derivatives of these positive clones. These clones have been given the laboratory designation pAOP1, pAOP2 and pAOP3 respectively.

d. Construction of plasmid pEGF819

Figure 8:
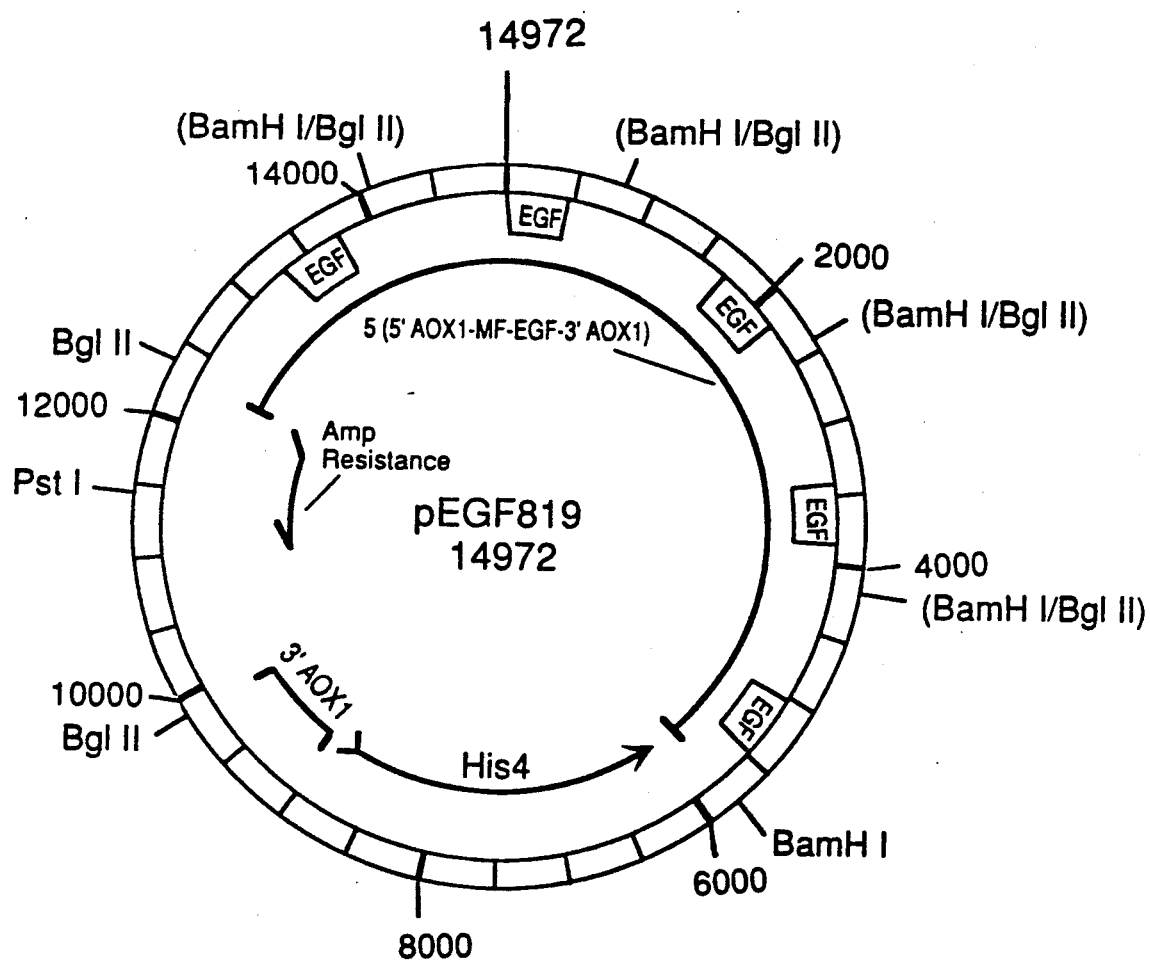
FIG. 8 is a restriction map of plasmid pEGF819.

Plasmid pEGF819 was constructed as follows:

Plasmid pAO817 was digested with BglII and BamHI and the 3600 bp fragment containing two expression cassettes was isolated on a 0.8% agarose gel. 250 ng of fragment and 25 ng of BamHI-cut phosphatase-treated pAO817 were ligated together. The ligation was used to transform MC1061 cells and Amp$^R$ cells were selected. DNA was prepared from the transformants and digested with BglII and BamHI. A 10,800 bp band, indicative of the fortuitous inclusion of two double cassettes fragments during ligation, was evident. The resulting plasmid was called pEGF819 and it contained five copies of the expression cassette in head-to-tail tandem. A restriction map of pEGF819 is shown in FIG. 8.

e. Construction of Plasmid pAO815

Figure 9:
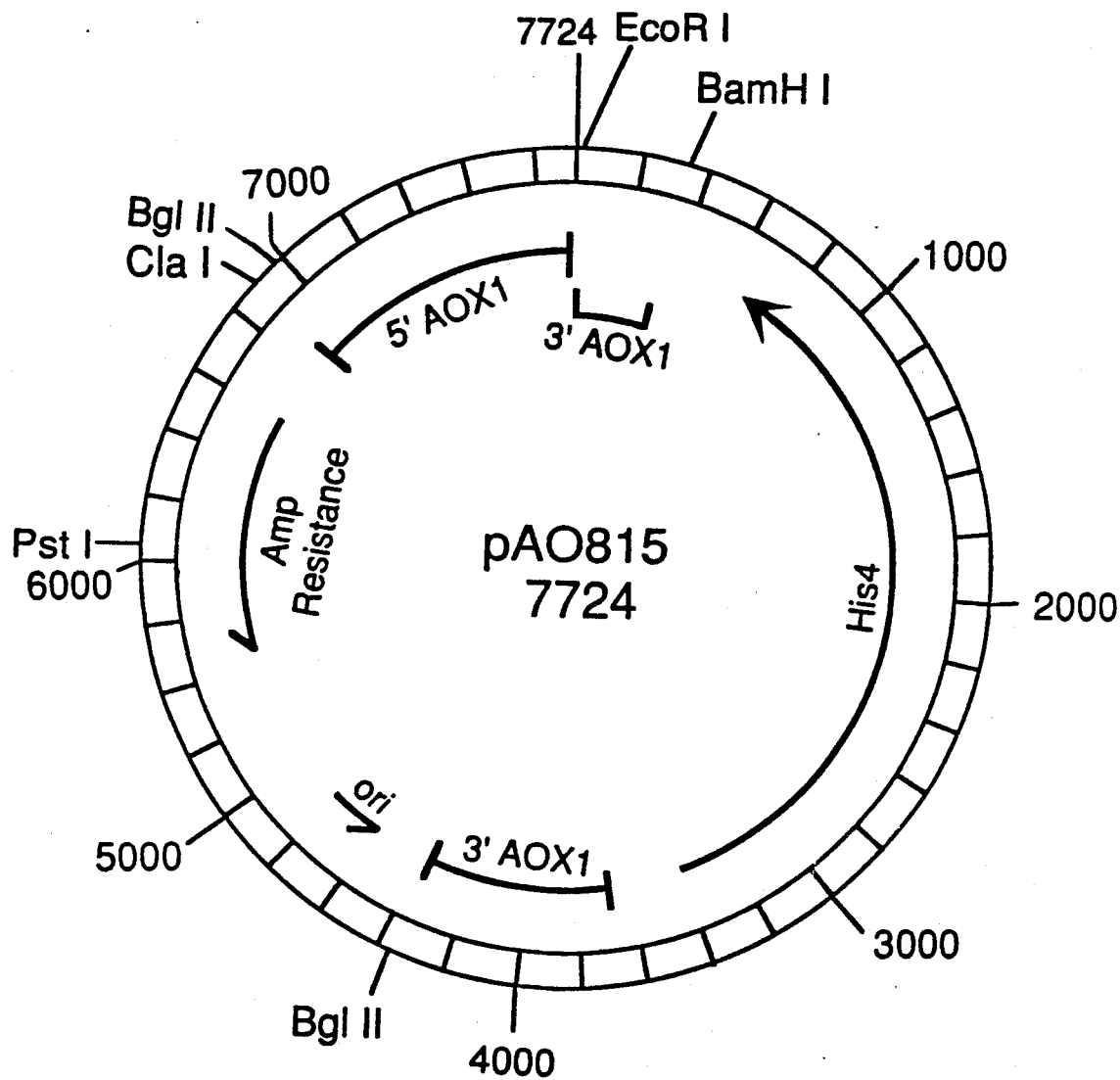
FIG. 9 is a restriction map of plasmid pA0815.

Plasmid pAO815 was constructed by mutagenizing plasmid pAO807 (described hereinbelow) to change the ClaI site downstream of the AOX1 transcription terminator in pAO807 to a BamHI site. The oligonucleotide used for mutagenizing pAO807 had the following sequence: 5' GAC GTT CGT TTG TGC GGA TCC AAT GCG GTA GTT TAT 3'. The mutagenized plasmid was called pAO807-Bam. Plasmid pAO804 was digested with BglII and 25 ng of the 2400 bp fragment were ligated to 250 ng of the 5400 bp BglII fragment from BglII-digested pAO807-Bam. The ligation mix was transformed into MC1061 cells and the correct construct was verified by digestion with Pst/BamHI to identify 6100 and 2100 bp sized bands. The correct construct was called pAO815. The restriction map of the expression vector pAO815 is shown in FIG. 9.

Plasmid pAO807 was constructed as follows:

1. Preparation of fl-ori DNA fl bacteriophage DNA (50 μg) was digested with 50 units of Rsa I and Dra I (according to manufacturer's directions) to release the ≈458 bp DNA fragment containing the fl origin of replication (ori). The digestion mixture was extracted with an equal volume of phenol:chloroform (V/V) followed by extracting the aqueous layer with an equal volume of chloroform and finally the DNA in the aqueous phase was precipitated by adjusting the NaCl concentration to 0.2M and adding 2.5 volumes of absolute ethanol. The mixture was allowed to stand on ice (4° C.) for 10 minutes and the DNA precipitate was collected by centrifugation for 30 minutes at 10,000×g in a microfuge at 4° C. The DNA pellet was washed 2 times with 70% aqueous ethanol. The washed pellet was vacuum dried and dissolved in 25 μl of TE buffer. This DNA was electrophoresed on 1.5% agarose gel and the gel portion containing the ≈458 bp fl-ori fragment was excised out and the DNA in the gel was electroeluted onto DE81 (Watman) paper and eluted from the paper in 1M NaCl. The DNA solution was precipitated as detailed above and the DNA precipitate was dissolved in 25 μl of TE buffer (fl-ori fragment).

2. Cloning of fl-ori into Dra I sites of pBR322 pBR322 (2 μg) was partially digested with 2 units Dra I (according to manufacturer's instructions). The reaction was terminated by phenol:chloroform extraction followed by precipitation of DNA as detailed in step 1 above. The DNA pellet was dissolved in 20 μl of TE buffer. About 100 ng of this DNA was ligated with 100 ng of fl-ori fragment (step 1) in 20 μl of ligation buffer by incubating at 14° C. for overnight with 1 unit of T4 DNA ligase. The ligation was terminated by heating to 70° C. for 10 minutes and then used to transform *E. coli* strain JM103. Amp$^R$ transformants were pooled and superinfected with helper phage R408. Single stranded phage were isolated from the media and used to reinfect JM103. Amp$^R$ transformants contained pBRfl-ori which contains fl-ori cloned into the Dra I sites (nucleotide positions 3232 and 3251) of pBR322.

3. Construction of plasmid pA0807 pBRfl-ori (10 μg) was digested for 4 hours at 37° C. with 10 units each of Pst I and Nde I. The digested DNA was phenol:chloroform extracted, precipitated and dissolved in 25 μl of TE buffer as detailed in step 1 above. This material was electrophoresed on a 1.2% agarose gel and the Nde I-Pst I fragment (approximately 0.8 kb) containing the fl-ori was isolated and dissolved in 20 μl of TE buffer as detailed in step 1 above. About 100 ng of this DNA was mixed with 100 ng of pA0804 (described hereinafter) that had been digested with Pst I and Nde I and phosphatase-treated. This mixture was ligated in 20 μl of ligation buffer by incubating for overnight at 14° C. with 1 unit of T4 DNA ligase. The ligation reaction was terminated by heating at 70° C. for 10 minutes. This DNA was used to transform *E. coli* strain JM103 to obtain pA0807.

Plasmid pA0804 employed in the above procedure was constructed as follows:

Plasmid pBR322 was modified as follows to eliminate the EcoRI site and insert a BglII site into the PvuII site:

pBR322 was digested with EcoRI, the protruding ends were filled in with Klenow Fragment of *E. coli* DNA polymerase I, and the resulting DNA was recircularized using T4 ligase. The recircularized DNA was used to transform *E. coli* MC1061 to ampicillin-resistance and transformants were screened for having a plasmid of about 4.37 kpb in size without an EcoRI site. One such transformant was selected and cultured to yield a plasmid, designated pBR322ΔRI, which is pBR322 with the EcoRI site replaced with the sequence:

5'-GAATTAATTC-3'

3'-CTTAATTAAG-5'.

pBR322ΔRI was digested with PvuII and the linker, of sequence

5'-CAGATCTG-3'

3'-GTCTAGAC-5' was ligated to the resulting blunt ends employing T4 ligase. the resulting DNAs were recircularized, also with T4 ligase, and then digested with BglII and again recircularized using T4 ligase to eliminate multiple BglII sites due to ligation of more than one linker to the PvuII-cleaved pBR322ΔRI. The DNAs, treated to eliminate multiple BglII sites, were used to transform *E. coli* MC1061 to ampicillin-resistance. Transformants were screened for a plasmid of about 4.38 kbp with a BglII site. One such transformant was selected and cultured to yield a plasmid, designated pBR322ΔRIBGL, for further work. Plasmid pBR322ΔRIBGL is the same as pBR322 RI except that pBR322ΔRIBGL has the sequence

5'-CAGCAGATCTGCTG-3'

3'-GTCGTCTAGACGAC-5' in place of the PvuII site in pBR322ΔRI.

pBR322ΔRIBGL was digested with a SalI and BglII and the large fragment (approximately 2.97 kbp) was isolated. Plasmid pBSAGI5I, which is described in European Patent Application Publication No. 0 226 752, was digested completely with BglII and XhoI and an approximately 850 bp fragment from a region of the *P. pastoris* AOX1 locus downstream from the AOX1 gene transcription terminator (relative to the direction of transcription from the AOX1 promoter) was isolated. The BglII-XhoI fragment from pBSAGI5I and the approximately 2.97 kbp, SalI-BglII fragment from pBR322ΔRIBGL were combined and subjected to ligation with T4 ligase. The ligation mixture was used to transform *E. coli* MC1061 to ampicillin-resistance and transformants were screened for a plasmid of the expected size (approximately 3.8 kbp) with a BglII site. This plasmid was designated pA0801. The overhanging end of the SalI site from the pBR322ΔRIBGL fragment was ligated to the overhanging end of the XhoI site on the 850 bp pBSAGI5I fragment and, in the process, both the SalI site and the XhoI site in pA0801 were eliminated.

pBSAGI5I was then digested with ClaI and the approximately 2.0 kbp fragment was isolated. The 2.0 kbp -15 fragment has an approximately 1.0-kbp segment which comprises the *P. pastoris* AOX1 promoter and transcription initiation site, an approximately 700 bp segment encoding the hepatitis B virus surface antigen ("HBsAg") and an approximately 300 bp segment which comprises the *P. pastoris* AOX1 gene polyadenylation signal and site-encoding segments and transcription terminator. The HBsAg coding segment of the 2.0 kbp fragment is terminated, at the end adjacent the 1.0 kbp segment with the AOX1 promoter, with an EcoRI site and, at the end adjacent the 300 bp segment with the AOX1 transcription terminator with a StuI site, and has its subsegment which codes for HBsAg oriented and positioned, with respect to the 1.0 kbp promoter-containing and 300 bp transcription terminator-containing segments, operatively for expression of the HBsAg upon transcription from the AOX1 promoter. The EcoRI site joining the promoter segment to the HBsAg coding segment occurs just upstream (with respect to the direction of transcription from the AOX1 promoter) from the translation initiation signal-encoding triplet of the AOX1 promoter.

For more details on the promoter and terminator segments of the 2.0 kbp, ClaI-site-terminated fragment of pBSAGI5I, see European Patent Application Publication No. 226,846 and Ellis et al., *Mol. Cell Biol.* 5, 1111 (1985).

Plasmid pA0801 was cut with ClaI and combined for ligation using T4 ligase with the approximately 2.0 kbp ClaI-site-terminated fragment from pBSAGI5I. The ligation mixture was used to transform *E. coli* MC1061 to ampicillin resistance, and transformants were screened for a plasmid of the expected size (approximately 5.8 kbp) which, on digestion with ClaI and BglII, yielded fragments of about 2.32 kbp (with the origin of replication and ampicillin-resistance gene from pBR322) and about 1.9 kbp, 1.48 kbp, and 100 bp. On digestion with BglII and EcoRI, the plasmid yielded an approximately 2.48 kbp fragment with the 300 bp terminator segment from the AOX1 gene and the HBsAg coding segment, a fragment of about 900 bp containing the segment from upstream of the AOX1 protein encoding segment of the AOX1 gene in the AOX1 locus, and a fragment of about 2.42 kbp containing the origin of replication and ampicillin resistance gene from pBR322 and an approximately 100 bp ClaI-BglII segment of the AOX1 locus (further upstream from the AOX1-encoding segment than the first mentioned 900 bp EcoRI-BglII segment). Such a plasmid had the ClaI fragment from pBSAGI5I in the desired orientation, in the opposite undesired orientation, there would be EcoRI-BglII fragments of about 3.3 kbp, 2.38 kbp and 900 bp.

One of the transformants harboring the desired plasmid, designated pA0802, was selected for further work and was cultured to yield that plasmid. The desired orientation of the ClaI fragment from pBSAGI5I in pA0802 had the AOX1 gene in the AOX1 locus oriented correctly to lead to the correct integration into the *P. pastoris* genome at the AOX1 locus of linearized plasmid made by cutting at the BglII site at the terminus of the 800 bp fragment from downstream of the AOX1 gene in the AOX1 locus.

pA0802 was then treated to remove the HBsAg coding segment terminated with an EcoRI site and a StuI site. The plasmid was digested with StuI and a linker of sequence:

5'-GGAATTCC-3'

3'-CCTTAAGG-5' was ligated to the blunt ends using T4 ligase. The mixture was then treated with EcoRI and again subjected to ligating using T4 ligase. The ligation mixture was then used to transform *E. coli* MC1061 to ampicillin resistance and transformants were screened for a plasmid of the expected size (5.1 kbp) with EcoRI-BglII fragments of about 1.78 kbp, 900 bp, and 2.42 kbp and BglII-ClaI fragment of about 100 bp, 2.32 kbp, 1.48 kbp, and 1.2 kbp. This plasmid was designated pA0803. A transformant with the desired plasmid was selected for further work and was cultured to yield pA0803.

Plasmid pA0804 was then made from pA0803 by inserting, into the BamHI site from pBR322 in pA0803, an approximately 2.75 kbp BglII fragment from the *P. pastoris* HIS4 gene. See, e.g., Cregg et al., *Mol. Cell. Biol.* 5, 3376 (1985) and European Patent Application Publication Nos. 180,899 and 188,677. pA0803 was digested with BamHI and combined with the HIS4 gene-containing BglII site-terminated fragment and the mixture subjected to ligation using T4 ligase. The ligation mixture was used to transform *E. coli* MC1061 to ampicillin-resistance and transformants were screened for a plasmid of the expected size (7.85 kbp), which is cut by SalI. One such transformant was selected for further work, and the plasmid it harbors was designated pA0804.

pA0804 has one SalI-ClaI fragment of about 1.5 kbp and another of abut 5.0 kbp and a ClaI-ClaI fragment of 1.3 kbp; this indicates that the direction of transcription of the HIS4 gene in the plasmid is the same as the direction of transcription of the ampicillin resistance gene and opposite the direction of transcription from the AOX1 promoter.

The orientation of the HIS4 gene is pA0804 is not critical to the function of the plasmid or of its derivatives with cDNA coding segments inserted at the EcoRI site between the AOX1 promoter and terminator segments. Thus, a plasmid with the HIS4 gene in the orientation opposite that of the HIS4 gene in pA0804 would also be effective for use in accordance with the present invention.

Example 2

Development of hEGF-secreting strains

1. Mut⁻ strains

20 μg of the expression vector pA0817 were digested with BglII, which releases the A0X1-ended tandem expression cassette. The linear DNA fragment obtained by digestion (5 μg) was transformed into the *P. pastoris* strain GS115 (ATCC 20864) by the spheroplast method [Cregg et al., *Mol. Cell. Biol.* 5, 3376 (1985)]. His+ cells were selected and the methanol utilization phenotype (Mut) of the cells was determined as follows:

His+ transformants were plated on minimal glucose (2%) master plates to obtain colonies originating from single cells. After overnight incubation at 30° C., the masters were replica-plated to minimal glucose plates and plates containing no carbon source to which methanol was added in vapor phase. This is accomplished by adding an aliquot, approximately 200 μl, of methanol to the underside of the top of a covered petri dish. The plates were incubated at 30° C. for 4-6 days with additional MeOH added in the vapor phase every two days. Colonies showing visible growth were scored as Mut+ add those with no visible growth were scored as Mut⁻.

Approximately 15% of the cells were His+Mut⁻, indicating that the expression vector integrated correctly at the AOX1 locus and disrupted the AOX1 gene. Southern analysis of an EcoRI digest of the transformants, using the plasmid pA0803 as probe, confirmed the disruption of the AOX1 gene and showed the number of expression units integrated. The strains were named as follows:

| Name | Site of Phenotype | Integration | Copy Number |
|---|---|---|---|
| G − EGF817S10 | Mut⁻His⁻ | AOX1 | One |
| G − EGF817S7 | Mut⁻His⁺ | AOX1 | One |
| G − EGF817S9 | Mut⁻His⁺ | AOX1 | Multiple |

In the above table copy number refers to the number of BglII fragments integrated. Each BglII fragment is comprised of two EGF expression cassettes.

2. Mut⁺ strains

*P. pastoris* strain GS115 (ATCC 20864) was transformed with 5 μg of uncut vector pA0817 using the spheroplast method of transformation. In this type of transformation the plasmid will integrate by addition into the *P. pastoris* genome at a site of homology between the plasmid and the host strain. The transformants were screened for His⁺Mut⁺ phenotype, and several were picked for Southern analysis. An EcoRI digest was probed with plasmid pYM4 [pYM4 was obtained by digesting pYM30 (NRRL B-15890) with ClaI and religating the ends] and the hybridization pattern revealed two of the six had appropriate integrations:

| Name | Site of Phenotype | Integration | Copy Number |
|---|---|---|---|
| G + EGF817S1 | Mut⁺His⁺ | HIS4 | One |
| G + EGF817S6 | Mut⁺His⁻ | HIS4 | One |

*P. pastoris* strain GS115 was transformed with 1 μg of uncut plasmid pEGF819 using the spheroplast method of transformation. The transformants were screened for His⁺ Mut⁺ phenotype and several were picked for Southern analysis as described for the Mut⁺ pAO817 transformants. Isolate G+EGF819S4 contained a set of four cassettes integrated at the 3' AOX1 locus.

Example 3

Fermentation of EGF strains a. Fermentor Start-Up and General Operation

The 2-liter fermentors (L.H. Fermentation, Hayward, Calif.; Biolafitte, LSL Biolafitte, Princeton, N.J.) were autoclaved at a 700 ml volume containing 225 ml of 10× basal salts (52 ml/l 85% phosphoric acid, 1.8 g/l Calcium Sulphate-2H₂O, 28.6 g/l Potassium Sulfate, 23.4 g/l Magnesium Sulfate-7H2O, 6.5 g/l Potassium Hydroxide) and 30 g glycerol. After sterilization, 3 ml of a YTM₄ trace salts solution (5.0 ml/l Sulfuric Acid, 65.0 g/l Ferrous Sulfate-7H₂O, 6.0 g/l Copper Sulfate-5H₂O, 20.0 g/l Zinc Sulfate-7H₂O, 3.0 g/l Manganese Sulfate-H₂O, 0.1 g/l Biotin) was added and the pH adjusted to 5.0 with the addition of concentrated Ammonium Hydroxide; the pH was then controlled at 5.0 with the addition of a 20% Ammonium Hydroxide solution containing 0.1% Struktol J673 antifoam (Struktol Co., Stow, Ohio) throughout the fermentation. Excessive foaming was controlled throughout the fermentation by addition of Struktol J693 antifoam when foam contacted a foam sensor in the fermentor. The fermentors were then inoculated with a 10-50 ml volume of inoculum (overnight shake flask culture in phosphate-buffered 0.65% Yeast Nitrogen Base, pH6, containing 2% glycerol). Upon exhaustion of the initial glycerol charge, a glycerol feed was started as described below. The dissolved oxygen of the fermentation was maintained above 20% of air saturation by increasing the air flow rate up to 3 liter/minute and agitation speed up to 1500 rpm during the fermentation.

Ten-liter fermentations (in a 15-liter Biolafitte fermentor) were started in a 7.0 liter volume containing 4 liters of 10× basal salts and 520 g of glycerol for the Mut⁺ methanol fed-batch protocol. After sterilization, 30 ml each of YTM₄ and IM₁ trace salts solutions were added and the pH was adjusted and subsequently controlled at 5.0 with the addition of ammonia gas throughout the fermentation. Excessive foaming was controlled with the addition of 5% Struktol J673 antifoam. The fermentor was inoculated with a volume of 200-500 ml. Upon exhaustion of the initial glycerol charge, a feed was started as outlined below. The dissolved oxygen was maintained above 20% by increasing the air flow rate up to 40 liter/minute, the agitation up to 1000 rpm and/or the pressure of the fermentor up to 1.5 bar during the fermentation.

b. Growth of Mut⁻ Strains in One-Liter Fermentors (1) Mut⁻ (NL) Mixed-Feed Fed Batch Fermentation Run 413:G-EGF817S10
Run 419:G-EGF817S9
Run 422:G-EGF817S9
Run 423:G-EGF817S10
Run 434:G-EGF817S9

After the glycerol batch phase was completed, a 50% (by weight) glycerol feed, containing 12 ml/l YTM₄ trace salts was started at 5.4 ml/h for the 2-liter fermentor. After 6 hours of glycerol feeding, the glycerol feed was decreased to 3.6 ml/h (36 ml/h at 10-liters) and a methanol feed containing 12 ml/l YTM4 trace salts was initiated at 1.1 ml/h for the 2-liter fermentor. After 5 hours, the methanol feed was adjusted to give a residual methanol concentration of up to about 1%, preferably between 0.2 and 0.8%. The fermentation was sampled periodically and harvested 36-50 hr after the methanol feed was initiated.

(2) Mut⁻ Methanol-Fed-Batch

Run 425:G-EGF817S9
Run 426:G-EGF817S10

After the glycerol batch phase was completed, an induced fed-batch phase was initiated by adding methanol to the fermentor to maintain a residual methanol concentration between 0.2 and 0.8%. The fermentor was sampled periodically and harvested after 167 hr growth on methanol.

(3) Alternative Procedure for Production of 1-52 hEGF

Run 470:G-EGF817S9

A two liter LH fermentor containing 400 ml 10X basal salts, 80 g glycerol, and deionized water (to 1 liter) was sterilized. After sterilization and cooling, 3 ml YTM₄+biotin solution was added and 20% NH₄OH used to bring pH to 3.6. The fermentor was inoculated with 60 ml of inoculum of Mut⁻ cells and the pH controller set at 5.0. During batch growth, the agitation speed was adjusted upward periodically to maintain a dissolved oxygen tension above 20% air saturation. After exhaustion of the initial glycerol charge, a 50% solution of glycerol containing 12 ml/l YTM₄+biotin was pumped into the fermentor at the rate of 20 ml/h. Four and one-half hours later, the glycerol feed rate was decreased to 10 ml/hr and a feed of methanol containing 12 ml/l YTM⁴+biotin was started at 1.0 ml/h. Three hours later the methanol feed rate was doubled. After ninety minutes at 2 ml/h, the methanol feed rate was adjusted to 3.8 ml/h and maintained constant until harvest at 13.5 hours after the methanol feed was first initiated.

c. Growth of Mut+ Strains in Two-Liter and 14-Liter Fermentors

Mut+ Methanol-Fed-Batch

Run 483:G+EGF819S4 (2L)
Run 464:G+EGF817S1 (2L)
Run 490:G+EGF819S4 (14L)

After glycerol exhaustion, a 50% glycerol feed, containing 12 ml/l YTM₄ trace salts, was started at 12 ml/h for the 2-liter or 200 ml/h for the 10-liter fermentor and run for a total of 7 hours. After 6 hours on the glycerol feed, the methanol feed, containing 12 ml/l YTM₄ trace salts, was started at 1.1 ml/h for the 2-liter and 11 ml/h for the 10-liter fermentor for 5 minutes. When a rise in dissolved oxygen was seen after the methanol feed was shut-off, the methanol feed was turned back on for another 5 minute interval. The latter process was repeated several times until an immediate response in the dissolved oxygen was observed to the methanol feed cessation; once this occurred, the methanol feed was increased by 20% per hour at 30 minute intervals. The methanol feed was increased until a feed rate of 7.6 ml/h for the 2-liter or 90 ml/h for the 10-liter fermentor was reached. The fermentation was then carried out for 40–60 hours for the 2-liter or 25–35 hours for the 10-liter fermentor.

Example 4

Results of Fermentations

Figure 10:
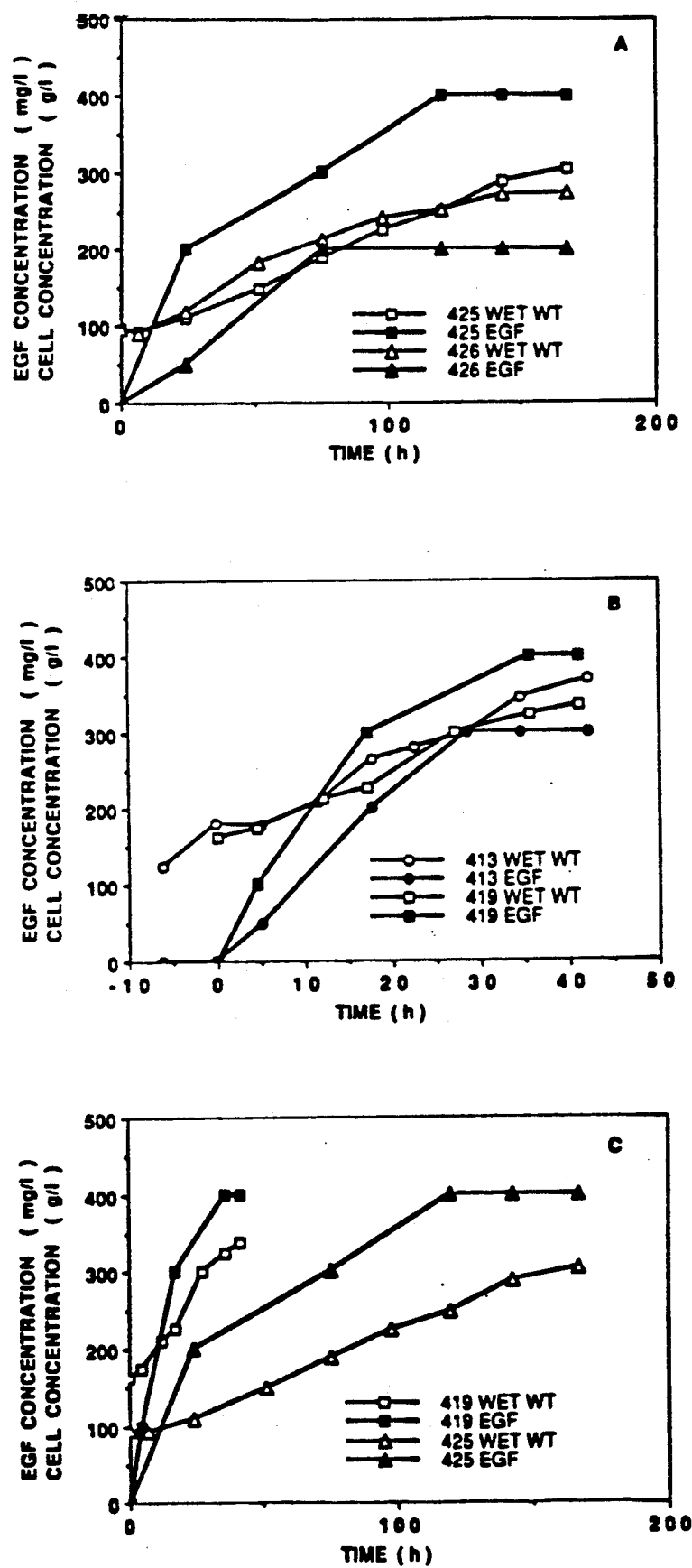
FIG. 10 shows the time course of cell growth and EGF expression in four fermentor runs. In all panels open symbols represent cell concentration and closed symbols represent EGF concentration.

FIG. 10 shows the time course of cell growth and EGF expression in four fermentor runs of two Mut⁻ strains. Panel A shows a comparison of the two strains grown under the methanol fed batch protocol. Cell growth for both strains was similar, yielding about 300 g/l wet cells after 167 h. However, the multicopy strain G-EGF817S9 produced 400 mg/l of EGF, twice as much as the strain with only two copies of the EGF expression cassette. The maximum concentration of EGF was reached after 120 hours growth on methanol.

Panel B shows a similar pattern for the two strains growing more rapidly under the mixed-feed protocol. In this protocol, both strains again grew up to more than 300 g/l, and the 400 mg/l of EGF produced by the multicopy strain is again higher than that produced by the double copy strain.

Panel C contrasts the two fermentations protocols with the multicopy strain, showing the reduced time on methanol required to produce EGF using mixed feed compared to using methanol alone, 35 hr vs. 120 hr, respectively. The initial batch growth on glycerol to build up cell mass adds another 24 h to the overall process time. The EGF productivities for the methanol and mixed feed modes are 3 mgl⁻¹h⁻¹ and 7 mgl⁻¹h⁻¹, respectively.

FIG. 11 shows a time course of hEGF production at both 1L (Run 483) and 10L (Run 490) volumes in fermentations employing the Mut+ strain G+EGF819S4. The higher hEGF production seen in these fermentations, 500–600 mg/L, as compared to the Mut⁻ fermentations is due to the higher copy number of G+EGF819S4 (4) rather than the Mut+ phenotype. A Mut+ strain carrying two copies of the EGF gene, G+EGF817S1, produced hEGF at concentrations similar to those seen in a Mut⁻ strain carrying two copies of the hEGF gene.

Example 5

Analysis of Secreted EGF

1. Western Analysis

The first mode of analysis for evaluation of Pichia-produced EGF was the Western blot. Because antisera against hEGF can have low cross-reactivity to mEGF, it was necessary to obtain human EGF standard and antisera, instead of mEGF and anti-mEGF, respectively, for our analyses. The human EGF reagents were acquired commercially from Amgen (standard) and Biomedical Technologies Inc., Stoughton, Mass. (antisera). Electrophoresis of broth samples was conducted on a 15% polyacrylamide gel. A typical Western blot showing samples taken from the last time point in all fermentor runs is seen in FIG. 12. Almost all the immunoreactive material was found in a single band which was of the same size as the human EGF standard. In several of the samples, (Runs 422, 423, 425), a larger molecular weight species, approximately 33 KD in size, was also seen to react with the antisera. By this analysis, the amount of EGF produced in runs with the multicopy strain appeared to be about twice as much as that produced in runs with the two copy strain.

2. Stained Gels

Protein bands on the acrylamide gels were also visualized by staining with Coomasie blue. FIG. 13 shows a stained gel of the same samples in FIG. 12. This gel is typical in that the primary protein species in the gel has an electrophoretic mobility similar to that of standard EGF. A further confirmation of the relative abundance of EGF protein in the broth was given by total protein assay of the broth. In the sample from Run 423, total TCA precipitable protein determined by the Lowry assay (100 mg/l±10 mg/l) was on the low end of the EGF concentration range estimated by Western blot with f-met-EGF standard 100–180 mg/l).

3. Separation of EGF Peptides on HPLC

Three peptides that eluted separately on reverse phase HPLC were purified to homogeneity by analytical HPLC. These peptides are designated with the numbers 1, 2, and 4 in the order of decreasing elution time. Approximately 50 μg of each peptide was obtained in a volatile buffer. Peaks 1 and 2 were purified from Run 470; Peak 4 was purified from Run 425. Peak 3 was not purified due to its relatively low concentration.

All three peaks were submitted to quantitative amino acid analysis after hydrolysis in 6N HCl containing 0.1% phenol. The compositions of hEGF Peaks 1 and 2 are consistent with an hEGF peptide that lacks a single arginine at the C-terminus. The composition of Peak 4, on the other hand, shows lower amounts of leucine and glutamic acid, and suggests decreased yields of lysine and aspartic acid. All three peptides, however, possess an authentic amino-terminus as determined by automated Edman degradation. This suggests that the difference in the composition of Peptide 4 results from alteration at its carboxy-terminus.

In an effort to determine the carboxy-terminal sequence of the peptides, they were each digested with carboxypeptidase Y (CPY) and the amino acids released over time were measured on an amino acid analyzer. FIG. 14 shows the results from the digestion of hEGF Peak 1. Since the most rapidly released amino acids were leucine followed by glutamic acid, it was concluded that Peak 1 is a 1-52 product of the originally translated peptide; the carboxy-terminal arginine was probably removed by proteolysis during fermentation. Peak 2 gave similar results as Peak 1, but Peak 4 did not yield any amino acids. This negative result was difficult to interpret, but could have been the result of a carboxy-terminal residue that is difficult for CPY to release, such as a lysine which occurs at position 48 of hEGF.

To determine if the tryptophan residues at positions 49 and 50 were absent in Peak 4, one microgram of each peptide (1,2,4) was submitted to reverse phase HPLC on a chromatography system equipped with a diode array detector (Hewlett Packard 1090). Absorbance at 280 nm and 210 nm was collected simultaneously for each peptide and the ratio 210 nm/280 nm was calculated both on the basis of peak height and integrated area. This ratio should be indicative of the tryptophan and tyrosine content of a peptide. More specifically, the ratio reflects the relative number of peptide bonds (contributors to 210 nm absorbance) to the number of tryptophan residues (contributors to 280 nm absorbance). tryptophan residues, when present in a sequence, tend to mask the smaller contribution of tyrosine to the absorbance at 280 nm.

The 210 nm/280 nm absorbance ratios of hEGF Peaks 1 and 2 were in the same range as those of other proteins that have a similar content of tryptophan. Peak 4, however, had a larger absorbance ratio which indicated the absence of any tryptophan residues. The unusually high number of tyrosine residues that remain in Peptide 4 depress the value of the absorbance ratio slightly.

The data from total amino acid analysis, N-terminal sequence, carboxypeptidase Y digestion, and UV absorbance ratios indicated that both Peaks 1 and 2 are 1-52 forms of hEGF while Peak 4 was a considerably shorter form.

The molecular weight of peptide 4 was subsequently determined by mass spectrometry and was consistent with an hEGF peptide comprised of residues 1-48. Carboxy peptidase digests of the peptide confirmed that the C-terminal peptide is the 48th residue, lysine.

4. Amino Acid Sequencing

Fractions containing the HPLC peaks at 22.47 min, 28.74 min, and 31.44 min were collected, and eight residues were sequenced on an automated gas phase protein microsequencer. Both the 22.47 min and 31.44 min peaks yielded the correct N-terminal sequence for EGF for the first eight residues. The peak at 28.74 min was not related to EGF.

5. Stability of Secreted EGF in Fermentation Broth of Pichia pastoris

HPLC analysis of hEGF in the broth during the time course of the fermentation runs revealed that the 1-48 peptide was much more stable than the longer forms. The longer forms could be seen early after induction during the run. After 24h growth on methanol, peptide 4 would accumulate, apparently as a degradation product of the other forms. Peptide 4 was very stable under fermentation conditions, persisting and accumulating for up to six days in the longer fermentation protocols. This unexpected high stability makes production and purification of this form of hEGF much simpler than that of the longer forms.

6. Biological Activity

The 1-48 hEGF peptide was tested for biological activity both in in vitro cell mitogenic assays and in vivo in stimulation of gastric ulcer healing. The peptide was observed to have high biological activity in both types of tests.

Example 6

Secretion of Invertase from *P. pastoris* a. Construction of Plasmid pSAMSU2

Plasmid pAMFD (or pTAMFSU1) is comprised of the αMF pre-pro sequence. The development of pAMFD is described hereinbelow. 25 μg of pAMFD was digested with EcoRI and HindIII following manufacturers' instructions. The digest was run on a 1% agarose gel, and the ≈1150 bp AMF-containing fragment was isolated. 10 μg of plasmid pSEYC306 (FIG. 15), comprised of the *S. cerevisiae* SUC2 gene was digested with EcoRI and HindIII following manufacturers' directions. Plasmid pSEYC306 is described in Johnson et al., *Cell* 48, 875 (1987). The 9.7 Kb plasmid fragment was extracted with phenol-chloroform and precipitated with ethanol. The ≈1150 bp fragment (≈10 μg) was ligated to ≈1 μg of the 9.7 Kbp vector fragment by T4 ligase, according to manufacturers' instructions. MC1061 cells were transformed with the ligation mixture, and ampicillin resistant colonies were selected. DNA was prepared from the amp$^r$ cells and digested with EcoRI and HindIII. Cells which yielded DNA demonstrating an ≈1150 bp EcoRI/HindIII fragment harbored plasmid of the correct orientation and were called pSAMSU1 (FIG. 16).

25 μg of pSAMSU1 was digested with PvuI and PvuII and the AMF prepro-SUC2 expression cassette was isolated on a 1% agarose gel as a ≈4200 bp fragment. 25 μg of pYJ30 (NRRL B-15890) was digested with EcoRI, filled in with Klenow, and digested with PvuI. The ≈6.4 bp PvuI-ended fragment contained the *P. pastoris* HIS4 gene. It was isolated on a 1% agarose gel and ligated to the ≈4200 bp PvuI/PvuII fragment. MC1061 cells were transformed with the ligation mix and amp$^r$ colonies were selected. DNA was prepared from the amp$^r$ cells and was digested with EcoRI and HindIII to demonstrate an ≈1150 bp fragment indicative of the AMF pre-pro segment, and with PvuII and NruI to demonstrate a 3140 bp fragment indicative of the HIS4 gene and PARSI. Plasmids demonstrating this pattern were called pSAMSU2 (FIG. 17).

Construction of Plasmid pAMFD

The alpha-factor genomic sequences were cloned by screening a library of yeast DNA sequences from Saccharomyces cerevisiae strain AB320 (HO, ade2-1, lys2-1, trp5-2, leu2-1, can1-100, ura3-1, ura1-1, met4-1). These genomic sequences are carried as a collection of Sau3A partials cloned into the BamHI site of YEp13. YEp13 is a yeast-*E. coli* shuttle vector capable of selection and replication in both yeast and *E. coli* and can be obtained from ATCC, accession number 37115. *E. coli* selection is provided by the ampicillin-resistance gene (beta-lactamase), while replication is accomplished using the origin of replication from pBR322. In yeast, selection is provided by the LEU2 gene. The wild type LEU2 gene provides enzymatic activity necessary to complement leu2-deficient strains, transforming them to leucine prototrophy. Replication in yeast derives from the 2μ circle origin of replication in yeast strains bearing a complete copy of the 2μ circle.

E. coli was transformed with YEp13 by using competent MC1061 cells and a heat shock step. Basically, cells are rendered competent by growing them to mid-log (OD600=0.3) and incubating them in cold 50 mM $CaCl_2$ at ½ the volume in which they were grown for 30 minutes on ice. They are centrifuged and resuspended in 1/50 the original volume of 10% glycerol, 50 mM $CaCl_2$ and aliquoted into 500 μl portions, stored in eppendorf tubes, quick frozen in liquid $N_2$ and stored at −70° C. To transform E. coli, an aliquot of competent MC1061 is thawed on ice. 100 μl of the cells are added to the DNA (10 ng in this case) and allowed to sit at 0° C. for 15 minutes. The cells are then placed at 37° C. for 5 minutes, followed by a 23° C. incubation. At this point, the cells are ready for selection. The frequency of transformation is approximately $10^3$ transformants/ng.

Transformants are identified by ampicillin resistance. Ampicillin resistance is determined by spreading the cells directly onto 1.5% agar plates containing L-broth (1% Bacto-Tryptone, 0.5% yeast extract, 1% sodium chloride) and 50 μg/ml ampicillin. The plates are then incubated at 37° C. Colonies which form at 37° C. after 16 hours are considered ampicillin-resistant. A collection of $10^4$ ampicillin-resistant colonies was obtained from the YEP13 library. Each plate was overlayed with 1 ml of L-broth containing 50 μg/ml ampicillin. The colonies were pooled, and the 5 ml volume was adjusted to 7% dimethyl sulfoxide (DMSO) and stored at −20° C.

Hybridization filters were prepared. The colonies were plated onto five plates (15 cm diameter) containing L-broth and 50 μg/ml ampicillin at a density of 4000 colonies per plate. Duplicate filters were prepared for hybridization as follows: A single 15 cm diameter nitrocellulose filter was placed over the plate and lifted up. This filter, which now contains the cells from the plate, serves as the master. The first filter is placed in contact with the master, and the filters are marked in three places to orient them with respect to each other. A second filter is separately placed over the master in the same fashion. The three filters are then placed (cell side up) on a 15 cm plate of 1.5% agar containing L-broth and 50 μg/ml of ampicillin and grown for 18 hours at 37° C. The next day the duplicate filters, but not the master (which is stored at 4° C.), are prepared for hybridization by placing them on stacks of Whatman filter paper soaked in 1.5M NaCl, 0.5M NaOH for 5 minutes and then submerging the filters in the same solution for 30 seconds. They are then submerged in 1M Tris-HCl, pH 8.0, 1.5M NaCl for 30 seconds. The filters are submerged in 2×SCC (0.3M NaCl, 0.03M Na citrate, pH 7.0) for 1 minute and allowed to air dry at room temperature for 20 minutes. They are then baked at 80° C. for 2 hours in a vacuum oven, after which they are ready for hybridization.

The prepared filters were probed with a 21 base probe having the sequence CGCAGCATTCTTC-GCATTAGC derived from the known sequence of alpha-factor (nucleotides 36-56 of the coding region) published by Kurjan and Herskowitz, Cell 30: 933 (1982). This probe was labeled with $^{32}P$ as follows: 100 ng of the oligonucleotide was incubated in a 50 μl reaction containing 50 mM Tris-HCl, pH 7.6, 10 mM $MgCl_2$, 5 mM dithiothreitol, 0.1 mM spermidine, 0.1 mM EDTA, 100 uCi of gamma-$^{32}P$ ATP (SA=7000 Ci/mmol) and 10 units of polynucleotide kinase at 37° C. for 30 minutes. The unincorporated radionucleotides were removed by gel filtration over Sephadex G-50 in 10 mM Tris-HCl, 1 mM EDTA, and the labeled oligonucleotide was stored in 10 mM Tris, 1 mM EDTA.

Prehybridization was performed at 42° C. in 6×SSPE (1×SSPE is 0.18M NaCl, 10 mM $NaPO_4$ pH 7.0, 1 mM EDTA) 10× Denhardt's (1× Denhardt's is 0.02% bovine serum albumin, 0.02% Ficoll, 0.02% polyvinylpyrollidone), 0.5% SDS for 3 hours. Hybridization was performed as above but with 10% dextran sulfate, $10^6$ cpm of probe per ml of hybridization, at 42° C. for 18 hours. The filters were washed with 2×SSC and 0.5% SDS at room temperature and exposed for 1 day at −70° C. with one intensifying screen to Kodak X-AR5 X-ray film. Seven positive colonies were identified.

Regions of a plate showing strong hybridization signals with the probe in duplicate were isolated and streaked on a 1.5% LB agar plate containing 50 μg/ml ampicillin. From this plate, single colonies were isolated and placed into wells of an 8×12 well microtiter dish containing 100 μl liquid LB+50 μg/ml ampicillin. After 18 h growth at 37° C., they were adjusted to 15% glycerol and stored at −70° C. A stamping device capable of transferring all colonies of an 8×12 well microtiter dish (96 wells) to a 15 cm filter grown on a 1.5% LB+50 μg/ml ampicillin plate was used to transfer single colony isolates from each positive hybridization region to a nitrocellulose filter in duplicate. These colonies were grown for 18 h at 37° C., and the filters were hybridized with the 21 base oligomer as described above. Four positive colonies were isolated in this manner and grown up in 2 ml liquid cultures of LB+50 μg/ml ampicillin [LB-AMP(50)] at 37° C. with agitation for 5-18 hours.

DNA was prepared from 1.5 ml of this culture by spinning the cells out and decanting the media. The cells were suspended in 100 μl of 50 mM glucose, 10 mM EDTA, 25 mM Tris-HCl, pH 8.0. They were allowed to sit on ice 5 minutes, after which 200 μl of 0.2N NaOH, 1% SDS was added, and the mixture was incubated 5 minutes at 0° C. To this mixture was added 150 μl of 3M sodium acetate, pH 5.2. After 10 minutes at 0° C., the tube was centrifuged for 10 minutes in a microfuge. The pellet was removed with a toothpick, and 400 μl of a 1:1 mixture of phenol chloroform (saturated with 10 mM Tris pH 7.5, 1 mM EDTA) was added. The aqueous layer (less than 400 μl) was removed after centrifugation, and 800 μl of 95% ethanol was added thereto. After incubation at −70° C. for 20 minutes, the sample was spun for 5 minutes in a microfuge. The pellet was washed with 1 ml of 95% ethanol, air dried and dissolved in 20-50 μl of 10 mM Tris-HCl, 1 mM EDTA, 10 μg/ml Ribonuclease A.

EcoRI restriction digests were performed by adding 1 μl of the mini-prepped DNA (200-500 ng) to the buffer prescribed by the manufacturer in a volume of 10 μl. The appropriate restriction enzyme was added at a concentration of 5-10 Units and the digest was incubated at 37° C. for 1-2 hours. The digest was analyzed by agarose gel electrophoresis (0.8-1.2%), and fragment sizes were quantitated by reference to known standards. Two colonies, AMFB and AMFD, had spectra similar to that published by Singh et al., *Nucl. Acids Res.* 22: 4049 (1983). They both had the 1.7 kb EcoRI fragment which should contain the promoter, structural gene and transcription terminator of alpha-factor.

b. Development of *P. pastoris* Transformant GS115(pSAMSU2)

*P. pastoris* strain GS115 was transformed with plasmid pSAMSU2 by the spheroplast transformation method. Spheroplasts generated from 5 $OD^{600}$ units of cells and 1 to 10 µg of pSAMSU2 plasmid were used. His+ transformants were selected and called GS115(pSAMSU2). Spheroplasts generated from 5 $OD^{600}$ units of cells of Pichia strain KM71 were likewise transformed with 1–10 µg of SAMSU2. His+ cells were selected and were called KM71(pSAMSU2). The development of strain KM71 is provided hereinbelow.

Development of Strain KM71

Pichia KM71 is a Pichia strain having the genotype: (his4 aox1::SARG4). This strain was created by transforming Pichia PPF1 (a his4 arg4 double auxotrophic mutant, available from the ATCC as 20865) with a linearized portion of plasmid pYMI7 [which contains the Saccharomyces ARG4 gene flanked by 3'- and 5'-Pichia alcohol oxidase gene (AOX1) sequences]. Plasmid pYMI7 was constructed by inserting a 2.9 kbp BamHI-SalI fragment from plasmid pYM25 (available in an *E. coli* host from the USDA, Northern Regional Research Center in Peoria, Ill., under the accession number NRRL B-18015, which plasmid contains the Saccharomyces ARG4 gene) into BamHI-cut ppg4.0 (available in an *E. coli* host from the USDA, Northern Regional Research Center in Peoria, Ill., under the accession number NRRL B-15868). The insertion results in a deletion of about 600 bp from the 5'-portion of the AOX1 gene (about one fourth of the gene). Plasmid pYMI7 was linearized by digestion with PvuII and EcoRI and transformed into PPF1 (arg4 his4) by selecting for Arg+ prototrophs. Transformants were extracted from the regeneration agar, sonicated and spread on SD medium agar plates containing 0.1% glucose and 40 µg/mL histidine. Colonies which resulted were then replica plated onto a set of SD medium agar plates (containing histidine) with the following carbon sources: 1) no carbon; 2) 0.5% methanol; and 3) 2% glucose. About 81.0% of the Arg+ colonies could not grow normally on methanol. Southern blot analysis of genomic DNA from one of the methanol nonutilizers confirmed that the AOX1 gene was disrupted in the strain designated as KM71.

c. Expression Studies

Strain GS115 (pSAMSU2) was grown in YNB with 2% glycerol as carbon source. The level of invertase was measured in the growth media from these cells and in the cells' periplasm. The data is represented in Table I.

TABLE I

αMF-DRIVEN INVERTASE EXPRESSION IN *P. PASTORIS*: MAXIMAL ACTIVITY LEVELS FOUND

| Host | Vector | Carbon Source | Invertase Activity Periplasm (U/OD$^{600}$) | Growth Medium (U/OD$^{600}$ · ml) |
|---|---|---|---|---|
| GS115 (P.p.) | pSAMSU2 | glycerol | 5.2 | 0.5 |
| KM71 (P.p.) | pSAMSU2 | glycerol | 5.6 | 0.4 |

1U = 1 µmole glucose produced in 1 minute at 37° C.
ND = not determined.

The invertase levels were usually higher in glycerol-grown cells than in methanol-grown cells. Invertase was assayed by the method described previously (Goldstein and Lampen, 1975).

Growth of cells in a 1L fermentor reached an $OD^{600}$ of 75 and invertase was secreted at a level of 13 mg/l, which represents approximately 28% of the total invertase expressed.

d. Characterization of Invertase

Secreted and periplasmic invertase from GS115 (pSAMSU2) was characterized by Western blot analysis before and after digestion wit Endo H. The antisera was raised in-house against deglycosylated *S. cerevisiae* invertase; Endo H was from New England Nuclear. *S. cerevisiae* invertase was obtained from Boehringer Mannheim and run in parallel as standard. Prior to Endo H treatment, the pSAMSU2-produced invertase migrated in SDS-PAGE as a heterogeneous species of 85–100 Kd, or as several discrete bands in the range of 85–100 Kd, whereas the standard invertase migrated as a smear at 100–140 Kd. It appeared as if the Pichia-produced product was less glycosylated than authentic *S. cerevisiae* invertase. This was confirmed by Endo H digestion. Both the pSAMSU2 and standard invertase collapsed to a single band in SDS-PAGE of 58 Kd after removal of sugars with Endo H. Because the migration distance of the recombinant and authentic invertase molecules (deglycosylated) appear identical, it is reasonable to assume that correct processing occurred at the AMF prepro-SCU2 junction [lys arg(glu-ala)$_2$-invertase].

We claim:

1. A *P. pastoris* cell containing in its genome at least one copy of a DNA sequence operably encoding an EGF peptide in *P. pastoris* in operational association with DNA sequence encoding the *S. cerevisiae* alpha-mating factor (AMF) pre-pro sequence, both under the regulation of a promoter region of a *P. pastoris* gene.

2. A *P. pastoris* cell according to claim 1, wherein said *P. pastoris* gene is the *P. pastoris* AOX1 gene.

3. A *P. pastoris* cell according to claim 2 containing at least two copies of said DNA sequences.

4. A *P. pastoris* cell according to claim 3 containing in its genome at least one copy of an expression cassette tandem consisting of two expression cassettes in head-to-tail orientation, each comprising in the direction of transcription, a promoter region of a first *P. pastoris* gene, DNA encoding the *S. cerevisiae* AMF pre-pro sequence, a DNA sequence encoding AMF processing-site lys-arg, DNA encoding an EGF peptide in *P. pastoris* and a transcription terminator of a second *P. pastoris* gene, said first and second *P. pastoris* genes being identical or different, the segments of said expression cassette being in operational association.

5. A *P. pastoris* cell according to claim 4 containing more than one copy of said expression cassette tandem.

6. A *P. pastoris* cell according to claim 4 wherein said first and second *P. pastoris* genes are identical and are the *P. pastoris* AOX1 gene.

7. A *P. pastoris* cell according to claim 4 containing a single copy of said expression cassette tandem integrated by replacement at the AOX1 locus of said *P. pastoris* genome.

8. A *P. pastoris* cell according to claim 5 containing multiple copies of said expression cassette tandem integrated by replacement at the AOX1 locus of said *P. pastoris* genome.

9. A *P. pastoris* cell according to claim 4 containing a single copy of said expression cassette tandem integrated by addition at the HIS4 locus of said *P. pastoris* genome.

10. A *P. pastoris* cell according to claim 5 containing three copies of said expression cassette tandem integrated by addition at the 3' AOX1 locus of said *P. pastoris* genome.

11. A *P. pastoris* cell according to claim 5 containing three copies of said expression cassette tandem integrated by addition at the 5' AOX1 locus of said *P. pastoris* genome.

12. A DNA fragment which is, or which is contained within. a circular plasmid, wherein said plasmid comprises at least one copy of an expression cassette comprising in the direction of transcription, a promoter region of a first *P. pastoris* gene, DNA encoding the *S. cerevisiae* AMF pre-pro sequence, a DNA sequence encoding AMF processing-site lys-arg, DNA encoding an EGF peptide in *P. pastoris* and a transcription terminator of a second *P. pastoris* gene, said first and second *P. pastoris* genes being identical or different, the segments of said expression cassette being in operational association.

13. A DNA fragment according to claim 12 containing two copies of said expression cassette in a head-to-tail-tandem.

14. A DNA fragment according to claim 12 containing six copies of said expression cassette in head-to-tail tandems.

15. A DNA fragment according to claim 12, wherein said first and second *P. pastoris* genes are identical and are the *P. pastoris* AOX1 gene.

16. A DNA fragment according to claim 15, further comprising a selectable marker gene and ends having sufficient homology with a target gene to effect integration of said DNA fragment therein.

17. A DNA fragment according to claim 16, which is a BglII digest of the Pichia expression vector pAO817.

18. A DNA fragment according to claim 16, which is the Pichia expression vector pEGF819.

19. An expression vector containing at least one copy of an expression cassette comprising in the direction of transcription, a promoter region of a first *P. pastoris* gene, DNA encoding the *S. cerevisiae* AMF pre-pro sequence, a DNA sequence encoding AMF processing-site lys-arg, DNA encoding an EGF peptide in *P. pastoris* and a transcription terminator of a second *P. pastoris* gene, said first and second *P. pastoris* genes being identical or different, the segments of said expression cassette being in operational association.

20. An expression vector according to claim 19 containing at least one tandem comprising two copies of said expression cassette in head-to-tail orientation.

21. An expression vector according to claim 20 containing one copy of said tandem.

22. An expression vector according to claim 20 containing said tandem in multiple copies.

23. An expression vector according to claim 22 containing three copies of said tandem.

24. An expression vector according to any one of claims 19 to 23, further comprising sequences allowing for its replication and selection in bacteria.

25. An expression vector according to claim 19, which is a pBR322 derivative.

26. An expression vector according to claim 25, which is the Pichia expression vector pAO817.

27. An expression vector according to claim 25, which is the Pichia expression vector pEGF819.

28. A culture of viable *P. pastoris* cells according to any one of claims 1 to 11.

29. A process for producing and secreting EGF peptides into the culture medium comprising growing *P. pastoris* transformants containing in their genome at least one copy of a DNA sequence operably encoding an EGF peptide in *P. pastoris* in operational association with DNA encoding the *S. cerevisiae* AMF pre-pro sequence, both under the regulation of a promoter region of a *P. pastoris* is gene, under conditions allowing the expression of said DNA sequences in said *P. pastoris* and secretion of the EGF product into the culture medium.

30. A process according to claim 29, wherein said *P. pastoris* transformants contain in their genome at least two copies of said NNA sequences.

31. A process according to cla:m 30, wherein said *P. pastoris* transformants contain in their genome at least one copy of an expression cassette tandem consisting of two expression cassettes in head-to-tail orientation, each comprising in the direction of transcription, a promoter region of a first *P. pastoris* gene, DNA encoding the *S. cerevisiae* AMF pre-pro sequence, a DNA sequence encoding AMF processing-site lys-arg, DNA encoding an EGF peptide in *P. pastoris* and a transcription terminator of a second *P. pastoris* gene, said first and second *P. pastoris* genes being identical or different, the segments of said expression cassette being in operational association.

32. A process according to claim 31, where said *P. pastoris* transformants contain in their genome more than one copy of said expression cassette tandem.

33. A process according to claim 29, wherein said transformants are obtained by transformation with a DNA fragment which is, or which is contained within, a circular plasmid, wherein said plasmid comprises at least one copy of an expression cassette comprising in the direction of transcription, a promoter region of a first *P. pastoris* gene, DNA encoding the *S. cerevisiae* AMF prepro sequence, a DNA sequence encoding AMF processing-site lys-arg, DNA encoding an EGF peptide in *P. pastoris* and a transcription terminator of a second *P. pastoris* gene, said first and second *P. pastoris* gene being identical or different, the segments of said expression cassette being in operational association.

34. A process according to claim 29, wherein said transformants are grown in a medium containing methanol as a carbon source.

35. A process according to claim 29, wherein said transformants are developed from the *P. pastoris* his4⁻ strain GS115.

36. A process according to claim 29 wherein said transformants have the Mut⁻ phenotype.

37. A process according to claim 29 wherein said transformants have the Mut⁻ phenotype.

38. A process according to claim 29 further comprising the step of harvesting said EGF from the culture medium.

39. A process according to claim 33 wherein said DNA fragment contains two copies of said expression cassette in a head-to-tail tandem.

40. A process according to claim 33 wherein said DNA fragment contains six copies of said expression cassette in head-to-tail tandems.

41. A process according to claim 33 wherein the first and second *P. pastoris* genes of said DNA fragment are identical and are the *P. pastoris* AOX1 gene.

42. A process according to claim 41, wherein said DNA fragment further comprises a selectable marker gene and ends having sufficient homology with a target gene to effect integration of said DNA fragment therein.

43. A process according to claim 42 wherein said DNA fragment is a Bgl II digest of the Pichia expression vector pAO817.

44. A process according to claim 42 wherein said DNA fragment is the Pichia expression vector pEGF819.

* * * * *

UNITED STATES PATENT AND TRADEMARK OFFICE
CERTIFICATE OF CORRECTION

PATENT NO. : 5,102,789                   Page 1 of 2
DATED : April 7, 1992
INVENTOR(S) : Siegel, et al.

It is certified that error appears in the above-identified patent and that said Letters Patent is hereby corrected as shown below:

On the title page, item (54):

In the Title, change "EPIDERAMAL" to --EPIDERMAL--.
    Under Other Publications, under "Shaw, et al.", change "cerdevisia" to --cerevisiae--, and change "preproseyquences" to --pre-pro sequences--.
    Under "Gregory et al.,", between "257" and "325" insert --,-- [comma].
    Under "Shuster", change "Yeat" to --Yeast--.

In column 1, line 1, change "EPIDERAMAL" to --EPIDERMAL--.
    In column 2, line 51, after "81", change "." [period] to --,-- [comma].
    In column 4, line 42, change "astoris" to --pastoris--.
    In column 7, line 13, after "Nature", change "." [period] to --,-- [comma].

In column 12, line 59, change "ppg2.0" to --pPG2.0-- (both occurrences).
    In column 13, line 65, change "ppg2.5" to --pPG2.5--.
    In column 13, line 67, change "ppg4.0" to --pPG4.0--.

UNITED STATES PATENT AND TRADEMARK OFFICE
CERTIFICATE OF CORRECTION

PATENT NO. : 5,102,789
DATED : April 7, 1992
INVENTOR(S) : Siegel, et al.

It is certified that error appears in the above-identified patent and that said Letters Patent is hereby corrected as shown below:

In column 16, line 64, delete "-15".
In column 18, line 64, change "add" to --and--.
In column 22, line 48, before "100" insert --(--.
In column 27, line 39, change "ppg4.0" to --pPG4.0--.
In column 28, line 27, change "wit" to --with--.

IN THE CLAIMS:
In Claim 29, line 8, delete "is".
In Claim 30, line 3, change "NNA" to --DNA--.
In Claim 37, line 2, change "Mut$^-$" to --Mut$^+$--.

Signed and Sealed this

Ninth Day of November, 1993

Attest:

BRUCE LEHMAN

Attesting Officer

Commissioner of Patents and Trademarks